(12) United States Patent
Julian et al.

(10) Patent No.: US 7,722,599 B2
(45) Date of Patent: May 25, 2010

(54) IN VIVO ACCESSORIES FOR MINIMALLY INVASIVE ROBOTIC SURGERY

(75) Inventors: Christopher A. Julian, Los Gatos, CA (US); Daniel T. Wallace, Redwood City, CA (US); Frederick H. Moll, Woodside, CA (US); Dean F. Hoornaert, Mountain View, CA (US); David J. Rosa, San Jose, CA (US); John G. Freund, Redwood City, CA (US); John W. Hill, Palo Alto, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 22 days.

(21) Appl. No.: 11/522,852

(22) Filed: Sep. 18, 2006

(65) Prior Publication Data

US 2007/0093792 A1    Apr. 26, 2007

Related U.S. Application Data

(60) Division of application No. 10/116,504, filed on Apr. 3, 2002, now Pat. No. 7,125,403, which is a continuation-in-part of application No. 09/478,953, filed on Jan. 7, 2000, now Pat. No. 6,770,081, which is a continuation-in-part of application No. 09/453,978, filed on Dec. 2, 1999, now Pat. No. 6,309,397.

(60) Provisional application No. 60/111,711, filed on Dec. 8, 1998.

(51) Int. Cl.
*A61B 17/00* (2006.01)

(52) U.S. Cl. ........................................ 606/1; 606/130

(58) Field of Classification Search .................. 606/1, 606/130, 41, 142, 143, 102, 78
See application file for complete search history.

(56) References Cited

U.S. PATENT DOCUMENTS

| 4,038,987 A | 8/1977 | Komiya |
| 4,899,730 A | 2/1990 | Stennert et al. |
| 5,186,714 A * | 2/1993 | Boudreault et al. ........... 604/21 |

(Continued)

OTHER PUBLICATIONS

Vertut, Jean and Coeffet, Philippe Coiffet; "Robot Technology; vol. 3A Teleoperation and Robotics Evolution and Development"; 1986; Prentice-Hall, Inc; Englewood Cliffs, N.J.

*Primary Examiner*—Pedro Philogene

(57) ABSTRACT

Surgical accessories are presented in vivo and used by surgical tools in the surgical site to perform additional tasks without the need to remove the tools from the surgical site for tool change or instrument loading. Examples of in vivo accessories include fastening accessories such as surgical clips for use with a clip applier, single working member accessories such as a blade which can be grasped and manipulated by a grasping tool for cutting, sheath accessories that fit over working members of a tool, flow tubes for providing suction or introducing a fluid into the surgical site, and a retraction member resiliently biased to retract a tissue to expose an area in the surgical site for treatment. The accessories can be introduced into the surgical site by a dedicated accessory introducer, or can be supported on the body of a surgical tool inserted into the surgical site and be manipulated using another surgical tool in the surgical site. The accessory introducer can be resiliently biased to bias the accessories toward a predetermined position in the surgical site.

9 Claims, 19 Drawing Sheet

U.S. PATENT DOCUMENTS

| | | | |
|---|---|---|---|
| 5,217,003 A | 6/1993 | Wilk | |
| 5,226,429 A | 7/1993 | Kuzmak | |
| 5,242,448 A * | 9/1993 | Pettine et al. | 606/102 |
| 5,368,015 A * | 11/1994 | Wilk | 600/104 |
| 5,417,210 A * | 5/1995 | Funda et al. | 600/425 |
| 5,503,320 A * | 4/1996 | Webster et al. | 227/176.1 |
| 5,634,937 A | 6/1997 | Mollenauer et al. | |
| 5,697,939 A * | 12/1997 | Kubota et al. | 606/130 |
| 5,762,458 A | 6/1998 | Wang et al. | |
| 5,792,135 A | 8/1998 | Madhani et al. | |
| 5,797,900 A | 8/1998 | Madhani et al. | |
| 5,808,665 A | 9/1998 | Green | |
| 5,814,038 A * | 9/1998 | Jensen et al. | 606/1 |
| 5,814,084 A * | 9/1998 | Grivas et al. | 623/23.48 |
| 5,855,583 A | 1/1999 | Wang et al. | |
| 5,876,325 A | 3/1999 | Mizuno et al. | |
| 6,159,200 A | 12/2000 | Verdura et al. | |
| 6,244,809 B1 | 6/2001 | Wang et al. | |
| 6,309,397 B1 | 10/2001 | Julian et al. | |
| 7,125,403 B2 * | 10/2006 | Julian et al. | 606/1 |

* cited by examiner

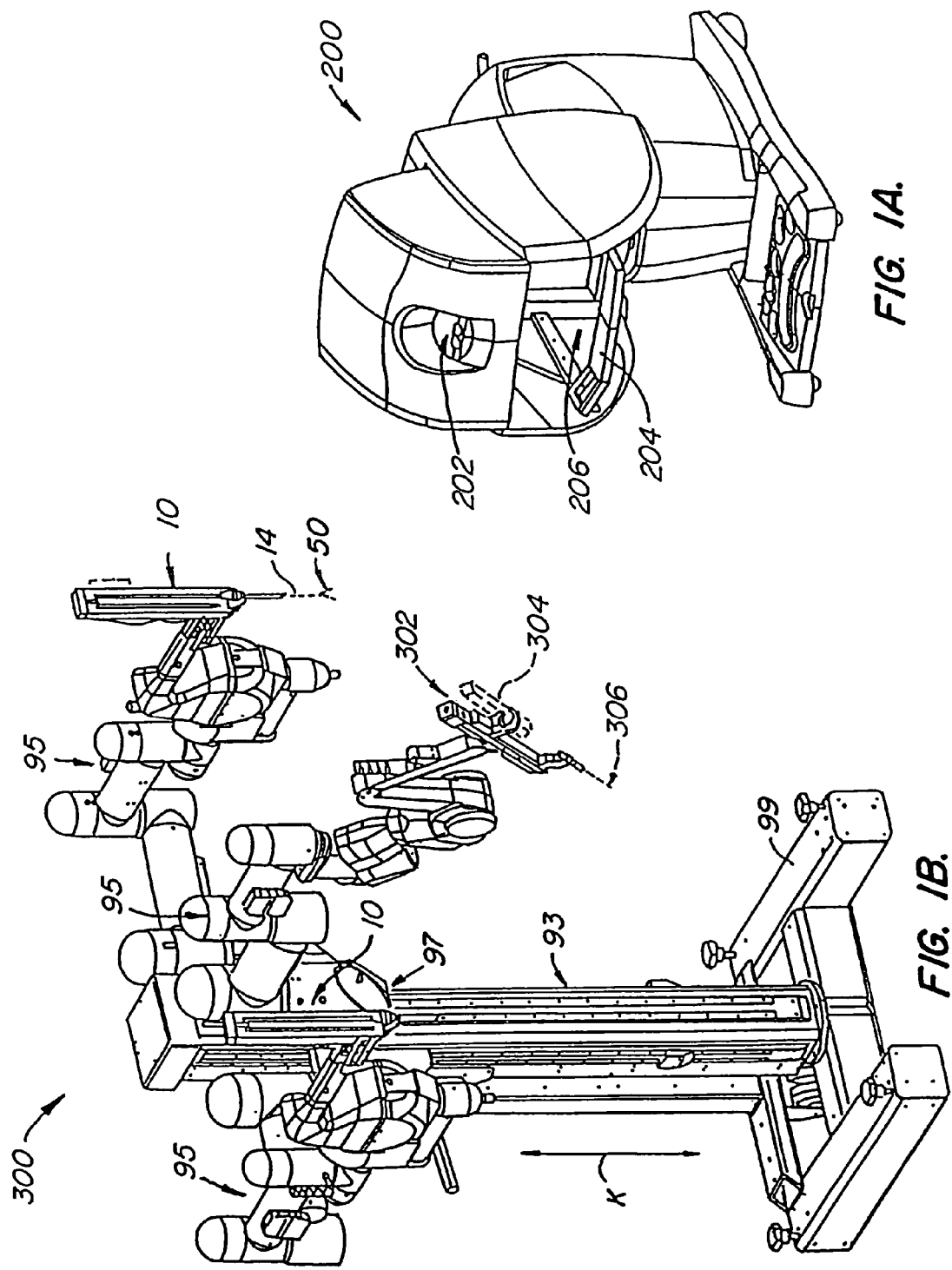

IN VIVO ACCESSORIES FOR MINIMALLY INVASIVE ROBOTIC SURGERY

CROSS-REFERENCES TO RELATED APPLICATIONS

This application is a divisional of 10/116504 now U.S. Pat. No. 7,125,403 filed Apr. 3, 2002 which is a continuation-in-part of and claims benefit from U.S. patent application Ser. No. 09/,478,953, filed Jan. 7, 2000 now U.S. Pat. No. 6,770,081, which is a continuation-in part of U.S. patent application Ser. No. 09/453978, filed Dec. 2, 1999 now U.S. Pat. No. 6,309,397, the complete disclosure of which is incorporated by reference.

This application is related to the following patents and patent applications, the full disclosures of which are incorporated herein by reference: PCT International Application No. PCT/US98/19508, entitled "Robotic Apparatus", filed on Sep. 18, 1998, U.S. application Ser. No. 09/418,726, entitled "Surgical Robotic Tools, Data Architecture, and Use", filed on Oct. 15, 1999; U.S. Application Ser. No. 60/111,711, entitled "Image Shifting for a Telerobotic System", filed on Dec. 8, 1998; U.S. application Ser. No. 09/378,173, entitled "Stereo Imaging System for Use in Telerobotic System", filed on Aug. 20, 1999; U.S. application Ser. No. 09/398,507, entitled "Master Having Redundant Degrees of Freedom", filed on Sep. 17, 1999, U.S. application Ser. No. 09/399,457, entitled "Cooperative Minimally Invasive Telesurgery System", filed on Sep. 17, 1999; U.S. Provisional application Ser. No. 09/373,678, entitled "Camera Referenced Control in a Minimally Invasive Surgical Apparatus", filed on Aug. 13, 1999; U.S. Provisional application Ser. No. 09/398,958, entitled "Surgical Tools for Use in Minimally Invasive Telesurgical Applications", filed on Sep. 17, 1999; and U.S. Pat. No. 5,808,665, entitled "Endoscopic Surgical Instrument and Method for Use", issued on Sep. 15, 1998.

BACKGROUND OF THE INVENTION

Advances in minimally invasive surgical technology could dramatically increase the number of surgeries performed in a minimally invasive manner. Minimally invasive medical techniques are aimed at reducing the amount of extraneous tissue that is damaged during diagnostic or surgical procedures, thereby reducing patient recovery time, discomfort, and deleterious side effects. The average length of a hospital stay for a standard surgery may also be shortened significantly using minimally invasive surgical techniques. Thus, an increased adoption of minimally invasive techniques could save millions of hospital days, and millions of dollars annually in hospital residency costs alone. Patient recovery times, patient discomfort, surgical side effects, and time away from work may also be reduced with minimally invasive surgery.

The most common form of minimally invasive surgery may be endoscopy. Probably the most common form of endoscopy is laparoscopy, which is minimally invasive inspection and surgery inside the abdominal cavity. In standard laparoscopic surgery, a patient's abdomen is insufflated with gas, and cannula sleeves are passed through small (approximately ½ inch) incisions to provide entry ports for laparoscopic surgical instruments. The laparoscopic surgical instruments generally include a laparoscope (for viewing the surgical field) and working tools. The working tools are similar to those used in conventional (open) surgery, except that the working end or end effector of each tool is separated from its handle by an extension tube. As used herein, the term "end effector" means the actual working part of the surgical instrument and can include clamps, graspers, scissors, staplers, and needle holders, for example. To perform surgical procedures, the surgeon passes these working tools or instruments through the cannula sleeves to an internal surgical site and manipulates them from outside the abdomen. The surgeon monitors the procedure by means of a monitor that displays an image of the surgical site taken from the laparoscope. Similar endoscopic techniques are employed in, e.g., arthroscopy, retroperitoneoscopy, pelviscopy, nephroscopy, cystoscopy, cisternoscopy, sinoscopy, hysteroscopy, urethroscopy and the like.

There are many disadvantages relating to current minimally invasive surgical (MIS) technology. For example, existing MIS instruments deny the surgeon the flexibility of tool placement found in open surgery. Most current laparoscopic tools have rigid shafts, so that it can be difficult to approach the worksite through the small incision. Additionally, the length and construction of many endoscopic instruments reduces the surgeon's ability to feel forces exerted by tissues and organs on the end effector of the associated tool. The lack of dexterity and sensitivity of endoscopic tools is a major impediment to the expansion of minimally invasive surgery.

Minimally invasive telesurgical robotic systems are being developed to increase a surgeon's dexterity when working within an internal surgical site, as well as to allow a surgeon to operate on a patient from a remote location. In a telesurgery system, the surgeon is often provided with an image of the surgical site at a computer workstation. While viewing a three-dimensional image of the surgical site on a suitable viewer or display, the surgeon performs the surgical procedures on the patient by manipulating master input or control devices of the workstation. The master controls the motion of a servo mechanically operated surgical instrument. During the surgical procedure, the telesurgical system can provide mechanical actuation and control of a variety of surgical instruments or tools having end effectors such as, e.g., tissue graspers, needle drivers, or the like, that perform various functions for the surgeon, e.g., holding or driving a needle, grasping a blood vessel, or dissecting tissue, or the like, in response to manipulation of the master control devices.

A typical surgery employs a number of different surgical instruments. When a different tool is desired during the surgical procedure, the surgical instrument is typically withdrawn from the surgical site so that it can be removed from its associated arm and replaced with an instrument bearing the desired end effector. The desired surgical instrument is then inserted into the surgical site.

A surgical instrument may also be withdrawn from a surgical site for reasons other than to replace the end effector. For example, the loading of a clip in a clip applier used in affixing tissue typically occurs outside of the patient's body. Each time a new clip is desired, the clip applier is removed from the surgical site to load the clip and then reintroduced into the patient's body to apply the clip. Tool exchange and instrument loading for a robotic system takes time. Providing additional surgical instruments in the surgical site (and the typically associated need to make additional incisions in the patient's body) may be an undesirable alternative for any number of reasons, e.g., due to space constraints, increase in system complexities, and/or cost.

SUMMARY OF THE INVENTION

The present invention is generally directed to robotic surgery methods, devices, and systems. The invention overcomes the problems and disadvantages of the prior art by providing surgical clips and/or other in vivo accessories at the surgical site. These in vivo accessories can be manipulated by robotic surgical tools in the site for performing different tasks. The accessories can be held by a dedicated accessory holder or support that is introduced into the surgical site through a separate opening. Alternatively, the accessories can be supported on the body of one of the surgical tools, and can be manipulated using another surgical tool in the surgical site. The surgical tools in the surgical site can use the accessories for performing a wide range of additional tasks without leaving the surgical site. In this way, the need to exchange tools and load instruments outside the surgical site is reduced, thereby minimizing "down time".

In accordance with an aspect of the present invention, a method of performing minimally invasive robotic surgery in a body cavity of a patient includes introducing at least one surgical accessory and a robotic surgical tool into the cavity. The surgical accessory is coupled with the robotic surgical tool inside the cavity after introducing the surgical accessory and the robotic surgical tool into the cavity. The surgical accessory may be decoupled from the robotic surgical tool inside the cavity.

In some embodiments, the robotic surgical tool is used to grasp the surgical accessory inside the cavity of the patient. In other embodiments, the surgical accessory is mated with the robotic surgical tool to form a mated connection. The surgical accessory may be coupled with the robotic surgical tool by introducing a second robotic surgical tool into the cavity and using it to facilitate coupling of the surgical accessory with the first surgical tool.

In certain preferred embodiments, the surgical accessory is introduced into the cavity supported by a surgical accessory support and the surgical accessory is removable from the surgical accessory support within the cavity. In a specific embodiment, the surgical accessory support includes a container. In another embodiment, the surgical accessory support includes a block having a material which deflects to releasably secure one or more surgical accessories therein. In yet another embodiment, the surgical support is provided on the body of another robotic surgical tool introduced into the cavity.

In a specific embodiment, a cartridge is introduced into the cavity to provide a plurality of surgical clips. The surgical tool is a clip applier. The clips are sequentially loaded in the clip applier within the cavity and the loaded clips are affixed to a target tissue with the clip applier.

In some embodiments, a portion of a master control device located remotely from the patient is actuated by a user to control the robotic surgical tool to grasp the surgical accessory. The robotic surgical tool may be instructed to continue to grasp the surgical accessory without requiring the user to continue to actuate the actuatable portion of the master control device.

In accordance with another aspect of the invention, a method of performing minimally invasive robotic surgery in a body cavity of a patient includes introducing a robotic fastening tool and a surgical accessory support into the cavity. The surgical accessory support supports a plurality of fastening accessories. One of the fastening accessories is loaded in the robotic fastening tool inside the cavity. The loaded fastening accessory is affixed to a target tissue inside the cavity with the robotic fastening tool.

In a specific embodiment, the robotic fastening tool is a clip applier and the fastening accessories include a plurality of surgical clips. The clips are supported on a clip cartridge or on the body of another robotic surgical tool introduced into the cavity.

Another aspect of the present invention is directed to a robotic surgical system for effecting a predetermined treatment of a target tissue at an internal surgical site within a patient body. The system includes a surgical accessory adapted for effecting the treatment, and an accessory introducer having a proximal end and a distal end with an opening therebetween. The distal end of the introducer is insertable into the patient body so that the opening defines a first minimally invasive aperture. The surgical accessory is coupled with the distal end of the introducer and is passable through the opening to the internal surgical site. A robotic arm supports a surgical tool having an end effector suitable for insertion through a second minimally invasive aperture to the internal surgical site. The end effector is coupleable with the surgical accessory within the internal surgical site so that the robot arm can manipulate the surgical accessory to direct the treatment to the target tissue.

In some embodiments, the accessory comprises a tool tip configured to be releasably coupled to an end effector working member of the surgical tool to form a tool tip for the end effector. In specific embodiment, the end effector comprises a pair of working members and the accessory comprises a pair of fingers movably supported on a collar which is configured to be releasably coupled with the surgical tool in a coupled position. The pair of fingers mate with the pair of working members to be movable by the pair of working members in the coupled position.

Another aspect of the invention is directed to an apparatus for providing a surgical accessory in vivo through a wall of a patient body into an internal cavity of the patient body for effecting a desired treatment of a target tissue in the patient body. The apparatus includes a surgical accessory adapted for effecting the treatment and an accessory introducer having a proximal end and a distal end with an opening therebetween. The distal end of the introducer is insertable into the patient body so that the opening defines a first minimally invasive aperture. The surgical accessory is coupled with the distal end of the introducer and passable through the opening to the internal cavity. A resilient member is connected with the accessory introducer to resiliently bias the surgical accessory to a preset desired location within the internal cavity.

In a specific embodiment, the accessory introducer includes a support member configured to be anchored to the wall of the patient body at the opening. A slidable member is coupled with the surgical accessory and is slidable relative to the support member. The resilient member includes a spring coupled between the support member and the slidable member.

In accordance with another aspect of the invention, a method of performing minimally invasive robotic surgery in an internal cavity of a patient body includes supporting a portion of a target tissue with a first robotic surgical tool introduced into the internal cavity. The first robotic surgical tool is electrically conductive. The method further includes contacting another portion of the target tissue with an electrically conductive cautery member introduced into the internal cavity. The first robotic surgical tool and the cautery member are energized for coagulating the target tissue. In some embodiments, the first robotic surgical tool and the cautery member are energized by connecting them to opposite leads of a radio frequency power source to form a bipolar system. In a specific embodiment, the cautery member is held by a second robotic surgical tool and electrically insulated therefrom.

In accordance with yet another aspect of the invention, a robotic surgical system for performing a procedure on a body comprises a surgical tool having an end effector including at least two end effector members, the members capable of grasping an object. A master control device has-an actuatable portion which is operatively connected to the surgical tool such that actuation of the portion causes the at least two end effector members to grasp the object. The system includes an input device for accepting an input from a user to cause the end effector members to continue to grasp without further actuation of the actuatable portion of the master control device.

BRIEF DESCRIPTION OF THE DRAWINGS

FIG. 1A is a perspective view of an operator station of a telesurgical system in accordance with an embodiment of the invention;

FIG. 1B is a perspective view of a cart or surgical station of the telesurgical system according to an embodiment of the invention, the cart of this particular embodiment carrying three robotically controlled arms, the movement of the arms being remotely controllable from the operator station shown in FIG. 1A;

DESCRIPTION OF THE SPECIFIC PREFERRED EMBODIMENTS

Figure 2A:
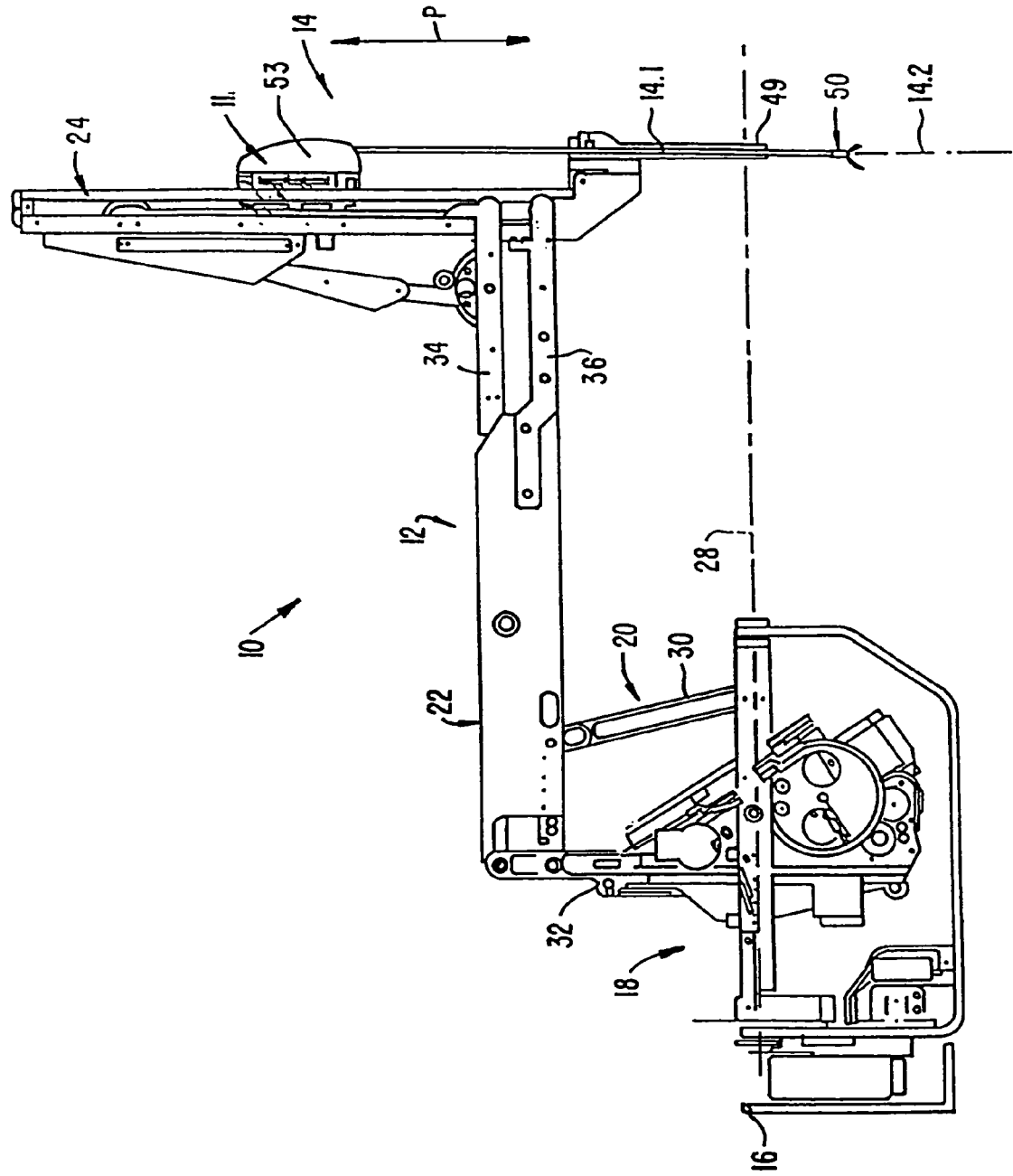
FIG. 2A is a side view of a robotic arm and surgical instrument assembly according to an embodiment of the invention.

As used herein, "end effector" refers to the actual working part that is manipulatable for effecting a predetermined treatment of a target tissue. For instance, some end effectors have a single working member such as a scalpel, a blade, or an electrode. Other end effectors have a pair of working members such as forceps, graspers, scissors, or clip appliers, for example.

As used herein, the terms "surgical instrument", "instrument", "surgical tool", or "tool" refer to a member having a working end which carries one or more end effectors to be introduced into a surgical site in a cavity of a patient, and is actuatable from outside the cavity to manipulate the end effector(s) for effecting a desired treatment of a target tissue in the surgical site. The instrument or tool typically includes a shaft carrying the end effector(s) at a distal end, and is preferably servo mechanically actuated by a telesurgical system for performing functions such as holding or driving a needle, grasping a blood vessel, and dissecting tissue.

As used herein, the terms "surgical accessory" and "accessory" refer to an assisting member that is introduced into the surgical site in the cavity of the patient to be used by an instrument or tool to perform a desired function in the surgical site.

One type of accessory is loaded in a surgical instrument and applied by the surgical instrument to a target tissue. For instance, fastening accessories are adapted to be used with a fastening tool for fastening tissues and the like. An example is a clip for use with a clip applier which affixes or anchors the clip to a target tissue. Another example is a suture needle with suture material for use with a suturing tool.

Another type of accessory is a single working member accessory such as a blade, a scalpel, a dissection finger, or an electrode, which does not require the more complex mechanisms for manipulating multiple working members such as forceps. For instance, a single working member accessory can be grasped by a tool having a pair of working members in a jaw-like arrangement, which is adapted for manipulating different single working member accessories and providing them with the desired degrees of freedom in movement to perform different treatments.

The accessory may be a tool tip that is configured to be releasably coupled to an end effector working member of the surgical tool to form a tool tip for the end effector. For an end effector having a pair of working members, the accessory may include a pair of fingers movably supported on a collar which is configured to be releasably coupled with the end effector in a coupled position. The pair of fingers mate with the pair of working members to be movable by the pair of working members in the coupled position.

The working members of a tool can be modified by sheath accessories. For instance, forceps on the working end of a tool can be fitted with insulating sheaths when desired to inhibit electric current leakage and prevent burning.

Another example of an accessory is a flow tube introduced into the cavity of the patient for providing suction, introducing a gas or a liquid, or transporting other matters into or out of the cavity. Such a flow tube can be grasped by a grasping tool inside the cavity and moved to the desired location for treating a particular area of the patient's body.

A retraction accessory includes a gripping portion such as a hook which can be manipulated by a grasping tool and used, e.g., to grip a tissue inside the surgical site. The retraction accessory is resiliently biased by a spring, preferably an adjustable spring, to move to a desired location, thereby retracting the tissue to expose an area in the surgical site for treatment. The retraction accessory preferably can be manipulated from inside or outside the body to further position tissue as desired, e.g., by providing a friction slide on the spring mechanism to adjust the spring preload. Further, a selection of springs of different tensions and spring constants may be provided to the surgeon depending upon the distances involved between the body wall and the tissue to be retracted.

I. Exemplary Telesurgical System

FIG. 1A shows an operator station or surgeon's console 200 of a minimally invasive telesurgical system. The station 200 includes a viewer 202 where an image of a surgical site is displayed in use. A support 204 is provided on which an operator, typically a surgeon, can rest his or her forearms while gripping two master controls (not shown in FIG. 1A), one in each hand. The master controls are positioned in a space 206 inwardly beyond the support 204. When using the control station 200, the surgeon typically sits in a chair in front of the control station 200, positions his or her eyes in front of the viewer 202 and grips the master controls one in each hand while resting his or her forearms on the support 204.

FIG. 1B shows a cart or surgical station 300 of the telesurgical system. In use, the cart 300 is positioned close to a patient requiring surgery and is then normally caused to remain stationary until a surgical procedure to be performed has been completed. The cart 300 typically has wheels or castors to render it mobile. The station 200 is typically positioned remote from the cart 300 and can be separated from the cart 300 by a great distance, even miles away, but will typically be used within an operating room with the cart 300.

The cart 300 typically carries three robotic arm assemblies. One of the robotic arm assemblies, indicated by reference numeral 302, is arranged to hold an image capturing device 304, e.g., an endoscope, or the like. Each of the two other arm assemblies 10 respectively, includes a surgical instrument 14. The endoscope 304 has a viewing end 306 at a remote end of an elongate shaft thereof. It will be appreciated that the endoscope 304 has an elongate shaft to permit its viewing end 306 to be inserted through an entry port into an internal surgical site of a patient's body. The endoscope 304 is operatively connected to the viewer 202 to display an image captured at its viewing end 306 on the viewer 202. Each robotic arm assembly 10 is normally operatively connected to one of the master controls. Thus, the movement of the robotic arm assemblies 10 is controlled by manipulation of the master controls. The instruments 14 of the robotic arm assemblies 10 have end effectors that are mounted on wrist members which are pivotally mounted on distal ends of elongate shafts of the instruments 14, as is described in greater detail below. It will be appreciated that the instruments 14 have elongate shafts to permit the end effectors to be inserted through entry ports into the internal surgical site of a patient's body. Movement of the end effectors relative to the ends of the shafts of the instruments 14 is also controlled by the master controls.

The robotic arms 10, 10, 302 are mounted on a carriage 97 by means of setup joint arms 95. The carriage 97 can be adjusted selectively to vary its height relative to a base 99 of the cart 300, as indicated by arrows K. The setup joint arms 95 are arranged to enable the lateral positions and orientations of the arms 10, 10, 302 to be varied relative to a vertically extending column 93 of the cart 300. Accordingly, the positions, orientations and heights of the arms 10, 10, 302 can be adjusted to facilitate passing the elongate shafts of the instruments 14 and the endoscope 304 through the entry ports to desired positions relative to the surgical site. When the surgical instruments 14 and endoscope 304 are so positioned, the setup joint arms 95 and carriage 97 are typically locked in position.

Figure 2B:
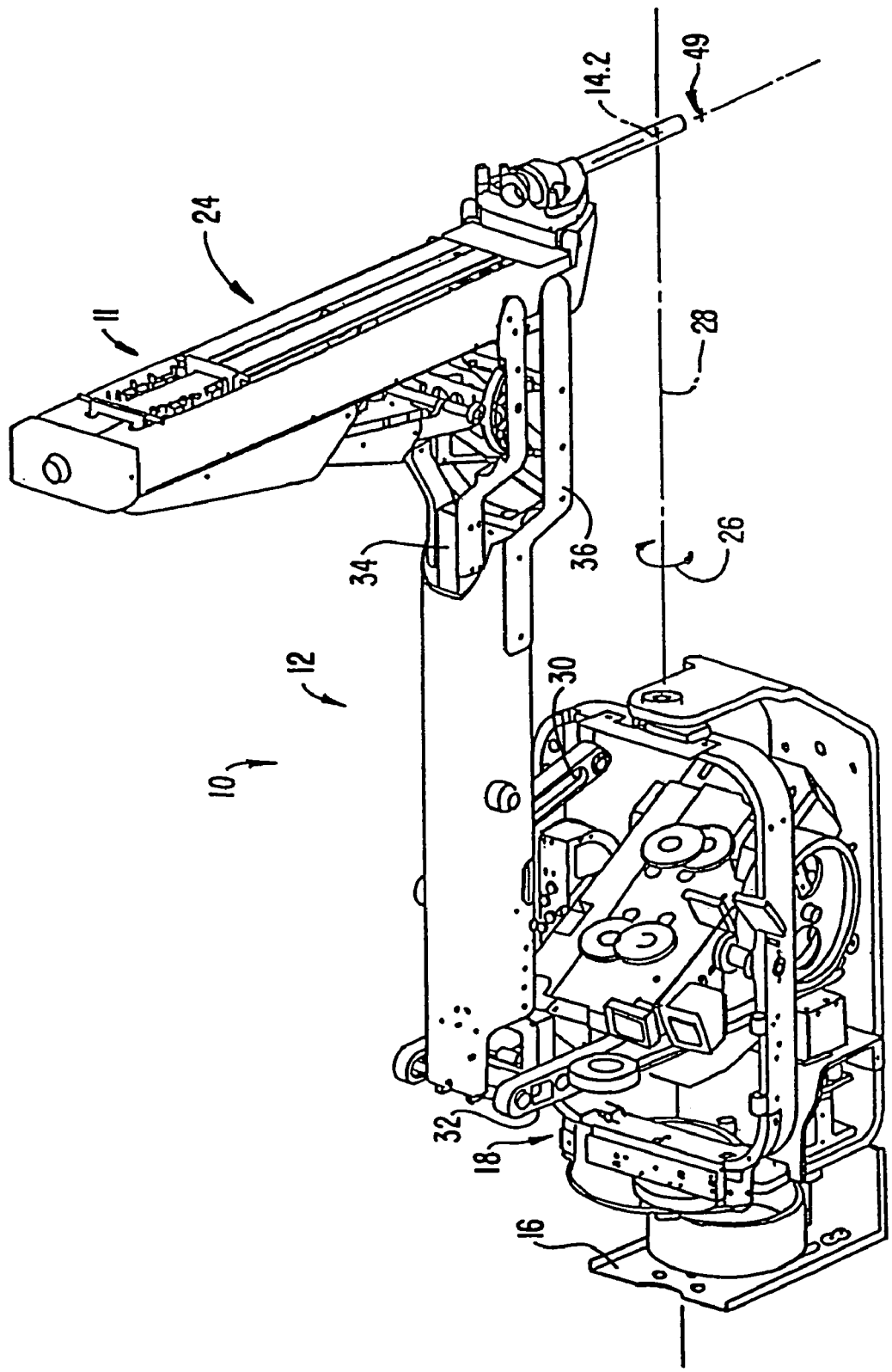
FIG. 2B is a perspective view of the robotic arm and surgical instrument assembly of FIG. 2A.
Figure 3:
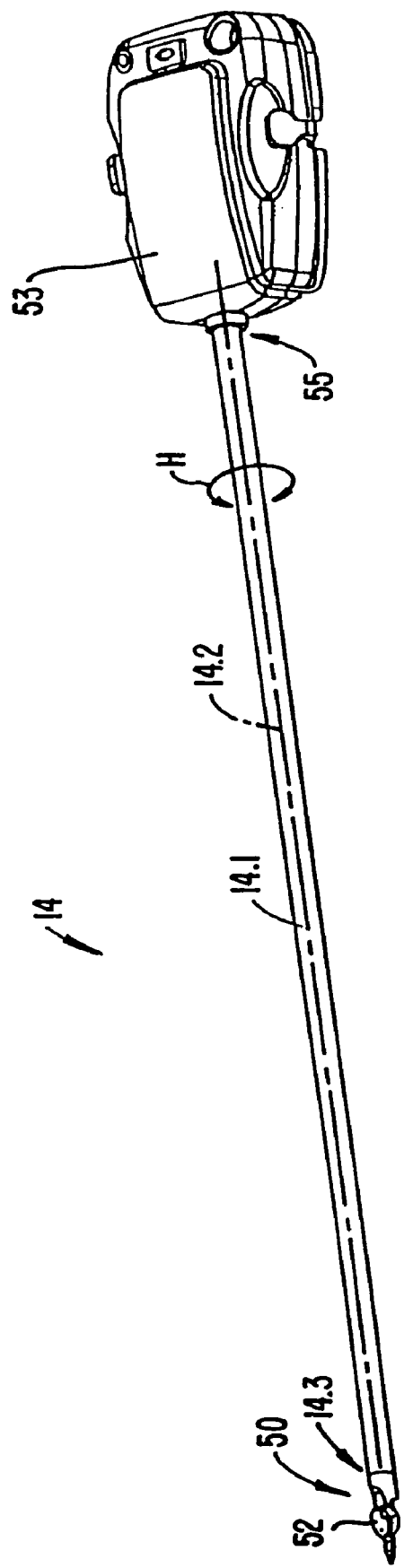
FIG. 3 is a perspective view of a surgical instrument according to an embodiment of the invention.

As shown in FIGS. 2A and 2B, each robotic arm assembly 10 includes an articulated robotic arm 12 and a surgical instrument 14 mounted thereon. As best seen in FIG. 3, the surgical instrument 14 includes an elongate shaft 14.1 and a wrist-like mechanism 50 located at a working end of the shaft 14.1. A housing 53, arranged releasably to couple the instrument 14 to the robotic arm 12, is located at an opposed end of the shaft 14.1. The shaft 14.1 is rotatably coupled to the housing 53 at 55 to enable angular displacement of the shaft 14.1 relative to the housing 53 as indicated by arrows H. In FIG. 2A, and when the instrument 14 is coupled or mounted on the robotic arm 12, the shaft 14.1 extends along an axis 14.2. The instrument 14 typically is releasably mounted on a carriage 11, which can be driven to translate along a linear guide formation 24 of the arm 12 in the direction of arrows P.

The robotic arm 12 is typically mounted on a base or platform at an end of its associated setup joint arm 95 by a bracket or mounting plate 16. The robotic arm 12 includes a cradle 18, an upper arm portion 20, a forearm portion 22, and the guide formation 24. The cradle 18 is pivotally mounted on the plate 16 in a gimbaled fashion to permit rocking movement of the cradle 18 in the direction of arrows 26 about a pivot axis 28 (FIG. 2B). The upper arm portion 20 includes link members 30, 32 and the forearm portion 22 includes link members 34, 36. The link members 30, 32 are pivotally mounted on the cradle 18 and are pivotally connected to the link members 34, 36. The link members 34, 36 are pivotally connected to the guide formation 24. The pivotal connections between the link members 30, 32, 34, 36, the cradle 18, and the guide formation 24 are arranged to constrain the robotic arm 12 to move in a specific manner.

Figure 4:
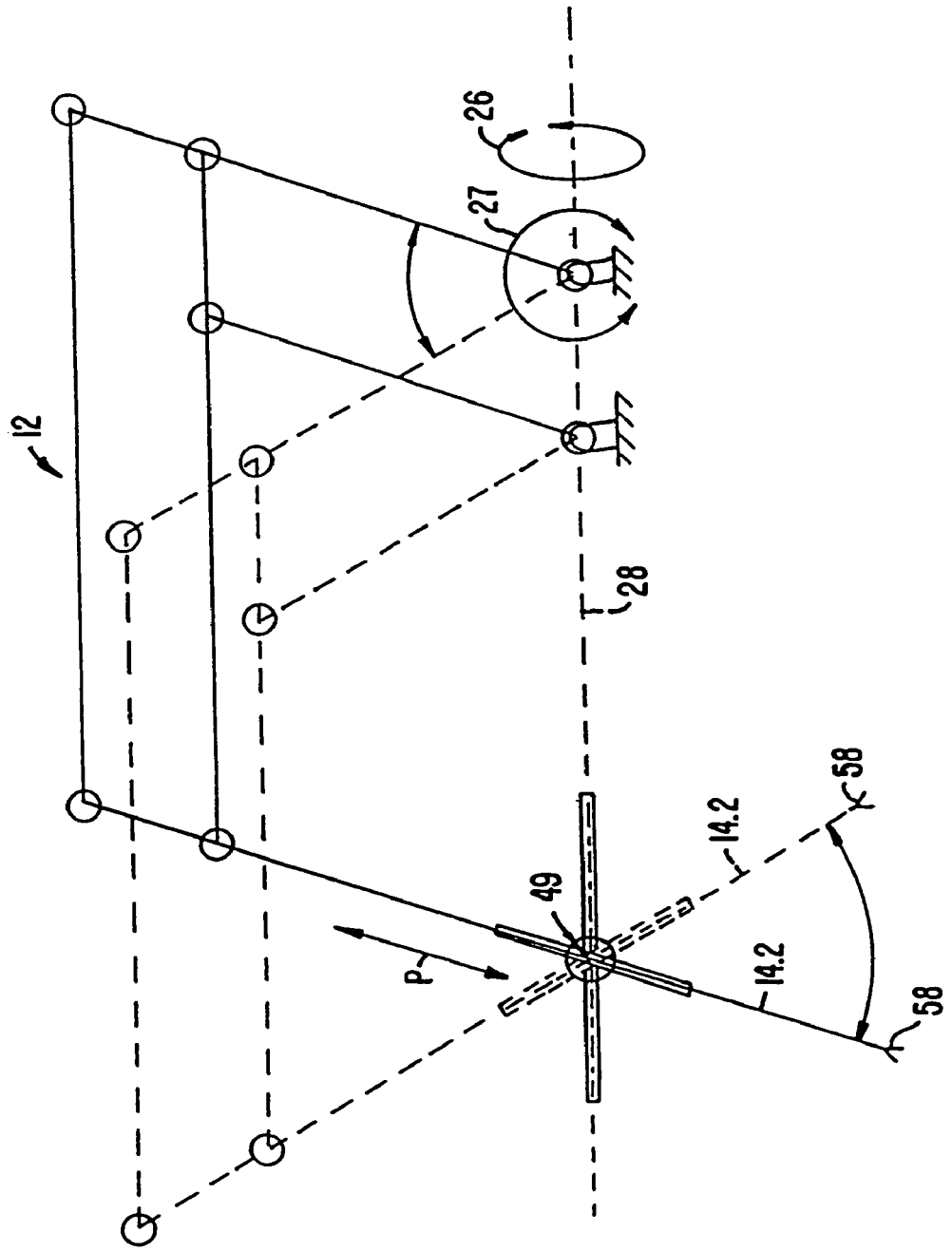
FIG. 4 is a schematic kinematic diagram corresponding to the side view of the robotic arm shown in FIG. 2A, and indicates the arm having been displaced from one position into another position.

The movements of the robotic arm 12 are illustrated schematically in FIG. 4. The solid lines schematically indicate one position of the robotic arm and the dashed lines indicate another possible position into which the arm can be displaced from the position indicated in solid lines.

It will be understood that the axis 14.2 along which the shaft 14.1 of the instrument 14 extends when mounted on the robotic arm 12 pivots about a pivot center or fulcrum 49. Thus, irrespective of the movement of the robotic arm 12, the pivot center 49 normally remains in the same position relative to the stationary cart 300 on which the arm 12 is mounted. In use, the pivot center 49 is positioned at a port of entry into a patient's body when an internal surgical procedure is to be performed. It will be appreciated that the shaft 14.1 extends through such a port of entry, the wrist-like mechanism 50 then being positioned inside the patient's body. Thus, the general position of the mechanism 50 relative to the surgical site in a patient's body can be changed by movement of the arm 12. Since the pivot center 49 is coincident with the port of entry, such movement of the arm does not excessively effect the surrounding tissue at the port of entry.

As can best be seen in FIG. 4, the robotic arm 12 provides three degrees of freedom of movement to the surgical instrument 14 when mounted thereon. These degrees of freedom of movement are firstly the gimbaled motion indicated by arrows 26, pivoting or pitching movement as indicated by arrows 27 and the linear displacement in the direction of arrows P. Movement of the arm as indicated by arrows 26, 27 and P is controlled by appropriately positioned actuators, e.g., electrical motors or the like, which respond to inputs from its associated master control to drive the arm 12 to a desired position as dictated by movement of the master control. Appropriately positioned sensors, e.g., potentiometers, encoders, or the like, are provided on the arm and its associated setup joint arm 95 to enable a control system of the minimally invasive telesurgical system to determine joint positions, as described in greater detail below. The term "sensors" as used herein is to be interpreted widely to include any appropriate sensors such as positional sensors, velocity sensors, or the like. By causing the robotic arm 12 selectively to displace from one position to another, the general position of the wrist-like mechanism 50 at the surgical site can be varied during the performance of a surgical procedure.

Figure 5:
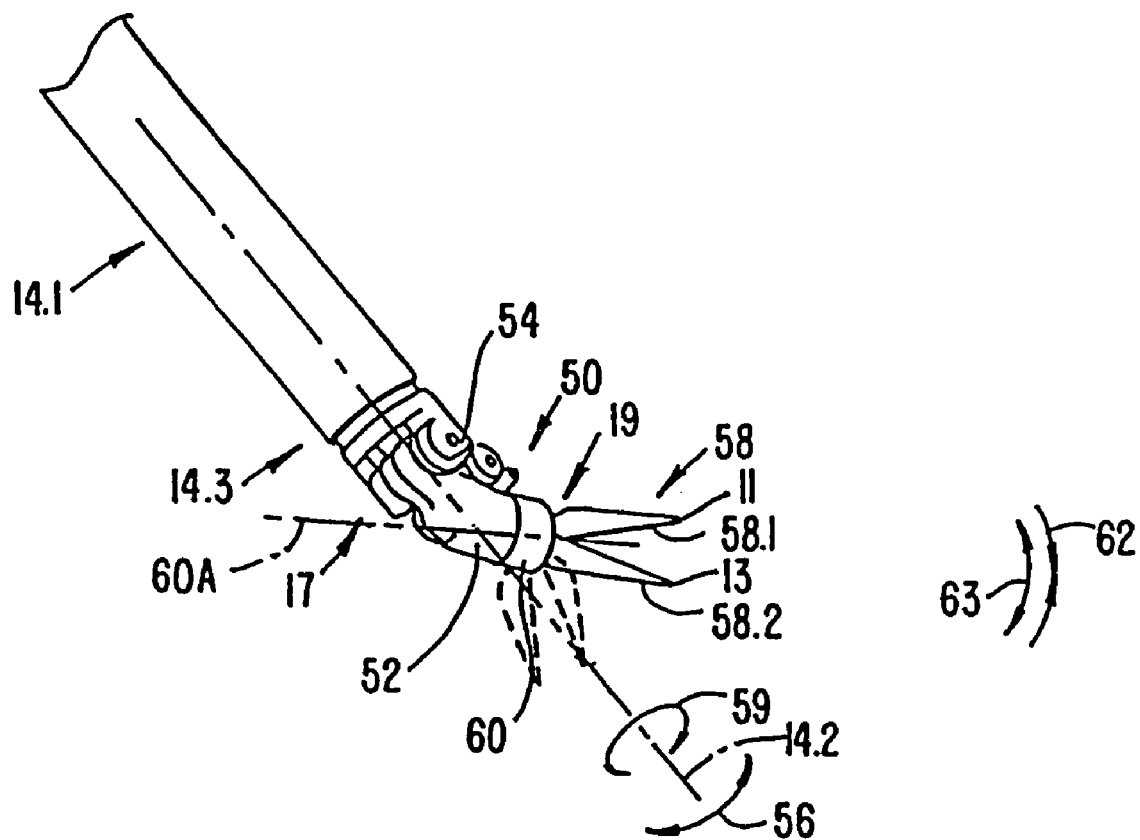
FIG. 5 is a perspective view of a wrist member and end effector of the surgical instrument shown in FIG. 3, the wrist member and end effector being movably mounted on a working end of a shaft of the surgical instrument.

Referring now to the wrist-like mechanism 50 of FIG. 5, the working end of the shaft 14.1 is indicated at 14.3. The wrist-like mechanism 50 includes a wrist member 52. One end portion of the wrist member 52 is pivotally mounted in a clevis 17 on the end 14.3 of the shaft 14.1 by means of a pivotal connection 54. The wrist member 52 can pivot in the direction of arrows 56 about the pivotal connection 54. An end effector 58 is pivotally mounted on an opposed end of the wrist member 52. The end effector 58 has two parts 58.1, 58.2 together defining a jaw-like arrangement.

The end effector can be in the form of any desired surgical tool, e.g., having two members or fingers which pivot relative to each other, such as a clip applier for anchoring clips, scissors, two-fingered blunt dissection tools, forceps, pliers for use as needle drivers, or the like. Moreover, it can include a single working member, e.g., a scalpel, cautery electrode, or the like. When a different tool is desired during the surgical procedure, the tool 14 is simply removed from its associated arm and replaced with an instrument bearing the desired end effector.

In FIG. 5, the end effector 58 is a grip applier. The end effector 58 is pivotally mounted in a clevis 19 on an opposed end of the wrist member 52, by means of a pivotal connection 60. The free ends 11, 13 of the parts 58.1, 58.2 are angularly displaceable about the pivotal connection 60 toward and away from each other as indicated by arrows 62, 63. The members 58.1, 58.2 can be displaced angularly about the pivotal connection 60 to change the orientation of the end effector 58 as a whole, relative to the wrist member 52. Thus, each part 58.1, 58.2 is angularly displaceable about the pivotal connection 60 independently of the other, so that the end effector 58, as a whole, is angularly displaceable about the pivotal connection 60 as indicated in dashed lines in FIG. 5. Furthermore, the shaft 14.1 is rotatably mounted on the housing 53 for rotation as indicated by the arrows 59. Thus, the end effector 58 has three degrees of freedom of movement relative to the arm 12 in addition to actuation of the end effector members to, e.g., grip tissue, namely, rotation about the axis 14.2 as indicated by arrows 59, angular displacement as a whole about the pivot 60 and angular displacement about the pivot 54 as indicated by arrows 56. By moving the end effector within its three degrees of freedom of movement, its orientation relative to the end 14.3 of the shaft 14.1 can selectively be varied. The movement of the end effector relative to the end 14.3 of the shaft 14.1 is controlled by appropriately positioned actuators, e.g., electrical motors, or the like, which respond to inputs from the associated master control to drive the end effector 58 to a desired orientation as dictated by movement of the master control. Furthermore, appropriately positioned sensors, e.g., encoders, or potentiometers, or the like, are provided to permit the control system of the minimally invasive telesurgical system to determine joint positions.

Figure 6A:
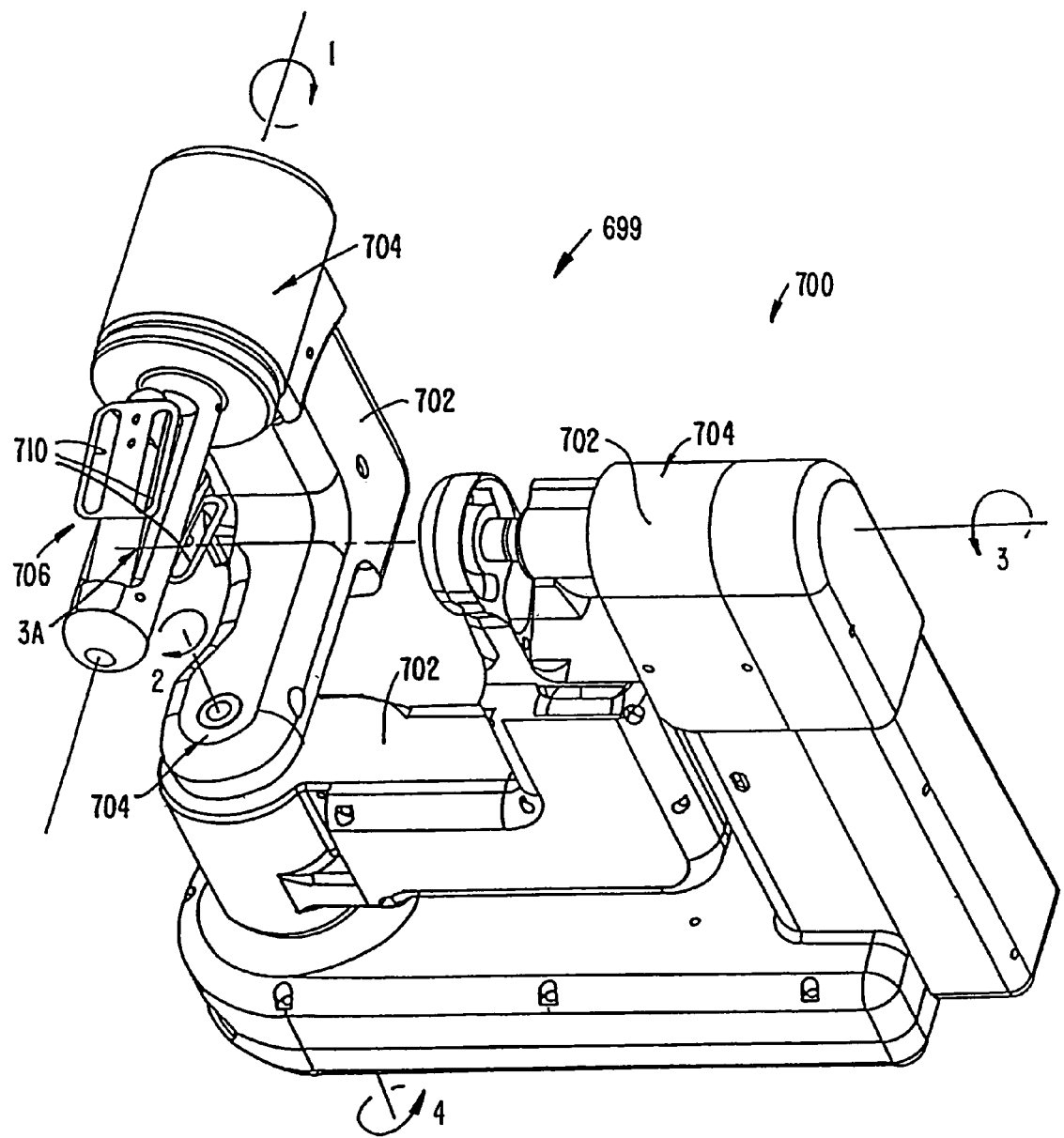
FIG. 6A is a perspective view of a hand held part or wrist gimbal of a master control device of the telesurgical system.
Figure 6B:
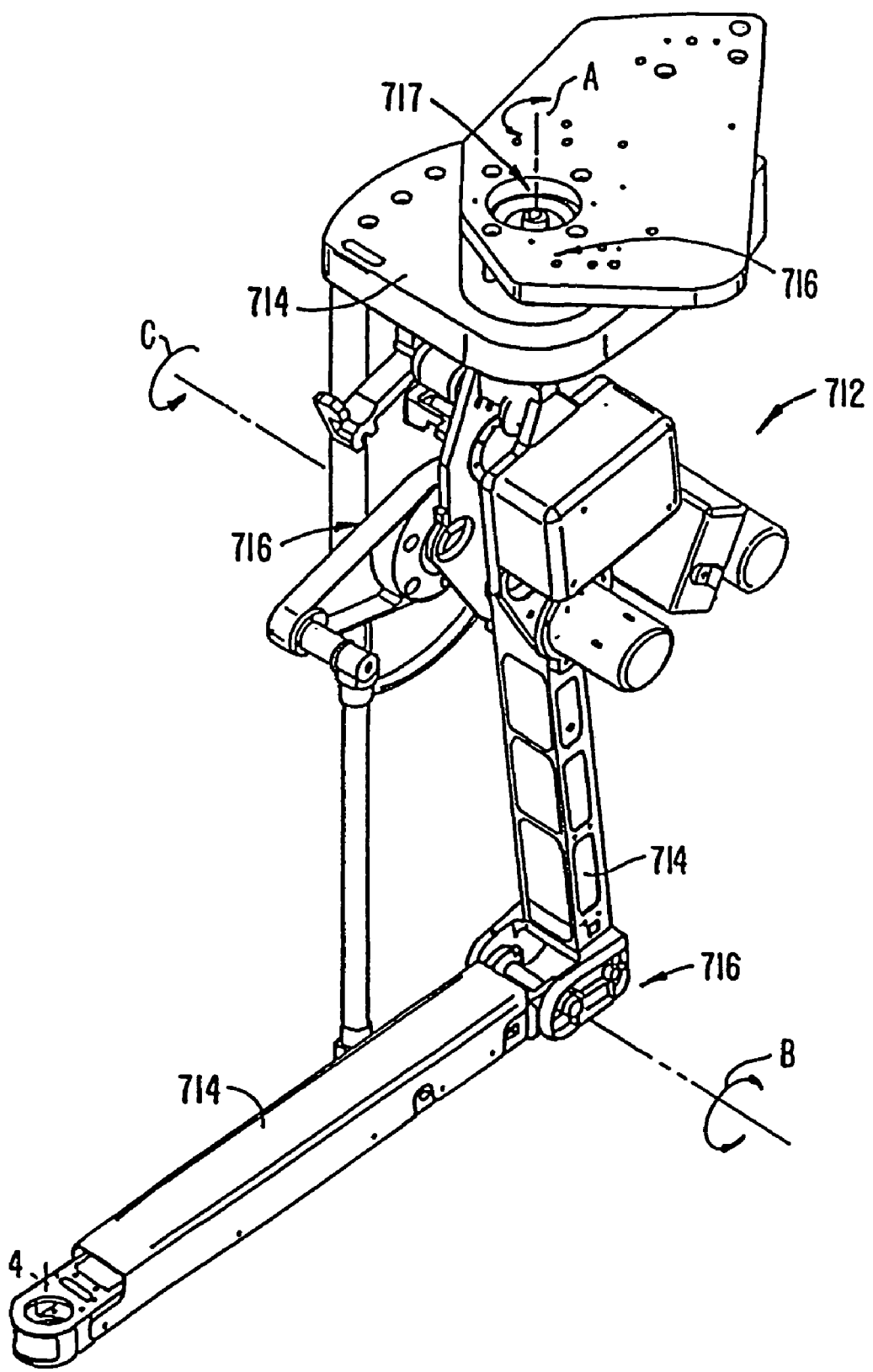
FIG. 6B is a perspective view of an articulated arm portion of the master control device of the telesurgical system on which the wrist gimbal of FIG. 6A is mounted in use.
Figure 6C:
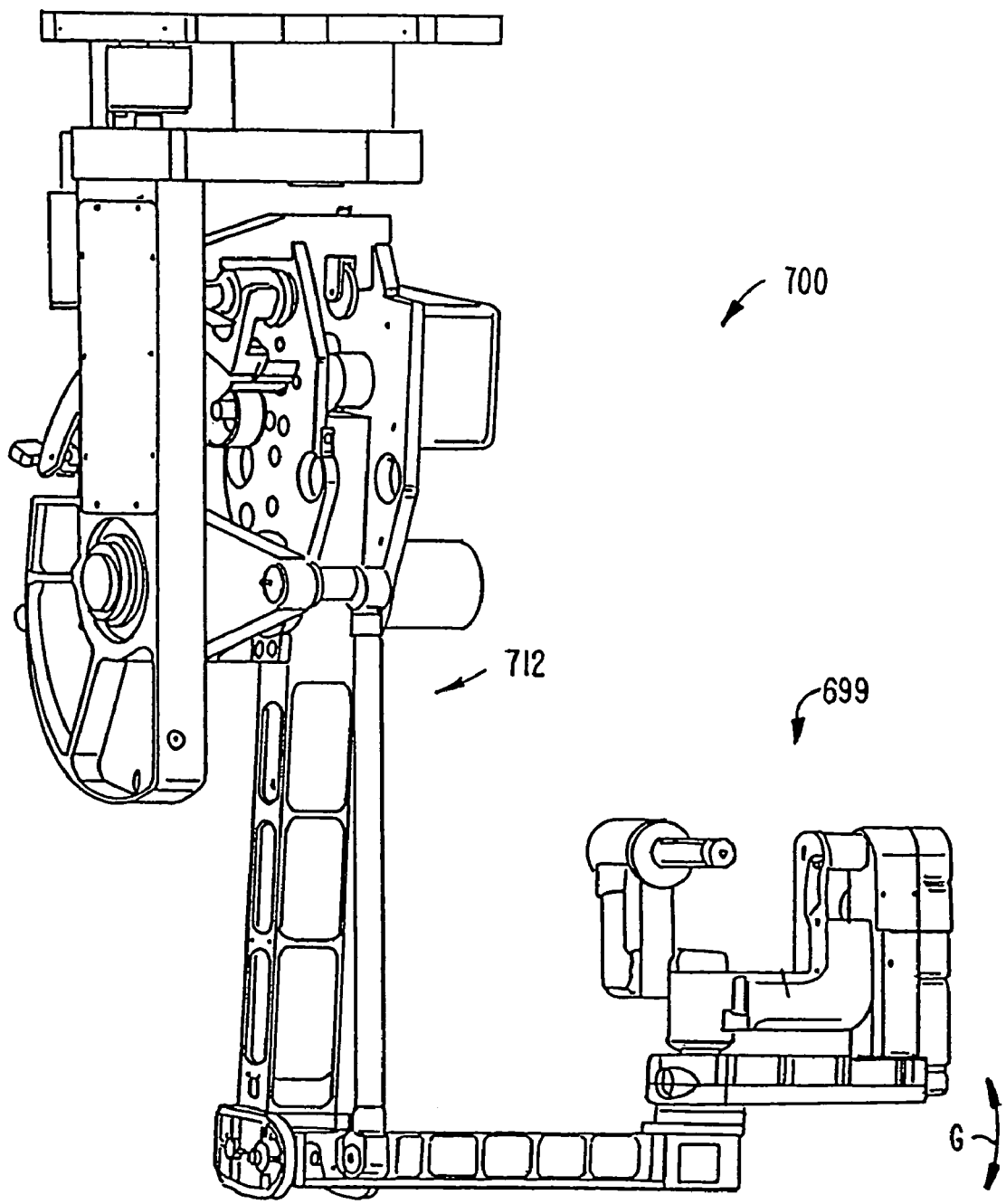
FIG. 6C is a perspective view of the master control device showing the wrist gimbal of FIG. 6A mounted on the articulated arm portion of FIG. 6B.

One of the master controls 700 is shown in FIG. 6C. As seen in FIG. 6A, a hand held part or wrist gimbal 699 of the master control device 700 has an articulated arm portion including a plurality of members or links 702 connected together by pivotal connections or joints 704. The surgeon grips the part 699 by positioning his or her thumb and index finger over a pincher formation 706. The surgeon's thumb and index finger are typically held on the pincher formation 706 by straps (not shown) threaded through slots 710. When the pincher formation 706 is squeezed between the thumb and index finger, the fingers or end effector elements of the end effector 58 close. When the thumb and index finger are moved apart the fingers of the end effector 58 move apart in sympathy with the moving apart of the pincher formation 706. The joints of the part 699 are operatively connected to actuators, e.g., electric motors, or the like, to provide for, e.g., force feedback, gravity compensation, and/or the like. Furthermore, appropriately positioned sensors, e.g., encoders, or potentiometers, or the like, are positioned on each joint 704 of the part 699, so as to enable joint positions of the part 699 to be determined by the control system.

The part 699 is typically mounted on an articulated arm 712 as indicated in FIG. 6B. Reference numeral 4 in FIGS. 6A and 6B indicates the positions at which the part 699 and the articulated arm 712 are connected together. When connected together, the part 699 can displace angularly about an axis at 4.

The articulated arm 712 includes a plurality of links 714 connected together at pivotal connections or joints 716. The articulated arm 712 further has appropriately positioned actuators, e.g., electric motors, or the like, to provide for, e.g., force feedback, gravity compensation, and/or the like. Furthermore, appropriately positioned sensors, e.g., encoders, or potentiometers, or the like, are positioned on the joints 716 so as to enable joint positions of the articulated arm 712 to be determined by the control system.

To move the orientation of the end effector 58 and/or its position along a translational path, the surgeon simply moves the pincher formation 706 to cause the end effector 58 to move to where he wants the end effector 58 to be in the image viewed in the viewer 202. Thus, the end effector position and/or orientation is caused to follow that of the pincher formation 706.

The master control devices 700, 700 are typically mounted on the station 200 through pivotal connections at 717 as indicated in FIG. 6B. As mentioned above, to manipulate each master control device 700, the surgeon positions his or her thumb and index finger over the pincher formation 706. The pincher formation 706 is positioned at a free end of the part 699 which in turn is mounted on a free end of the articulated arm portion 712.

The electric motors and sensors associated with the robotic arms 12 and the surgical instruments 14 mounted thereon, and the electric motors and sensors associated with the master control devices 700 are operatively linked in the control system. The control system typically includes at least one processor, typically a plurality of processors, for effecting control between master control device input and responsive robotic arm and surgical instrument output and for effecting control between robotic arm and surgical instrument input and responsive master control output in the case of, e.g., force feedback. An example of a suitable control system is described in U.S. application Ser. No. 09/373,678, entitled "Camera Referenced Control in a Minimally Invasive Surgical Apparatus", filed on Aug. 13, 1999.

II. In Vivo Accessories

To minimize the need to remove tools from the surgical site for tool replacement or instrument loading, the present invention provides ways to present a variety of accessories in vivo. The surgeon can manipulate these in vivo accessories using tools already in the surgical site and adapt them for performing different functions without the need to remove the tools from the surgical site. A number of examples of in vivo accessories are provided herein below.

A. Instrument Loading Accessories

Certain instruments are used by loading accessories specifically adapted for use with the particular instruments to perform the intended tasks. For example, fastening accessories such as clips are specifically adapted for use with a clip applier. The clips are loaded in a clip applier which affixes or anchors the clips one at a time to a target tissue.

Figure 7:
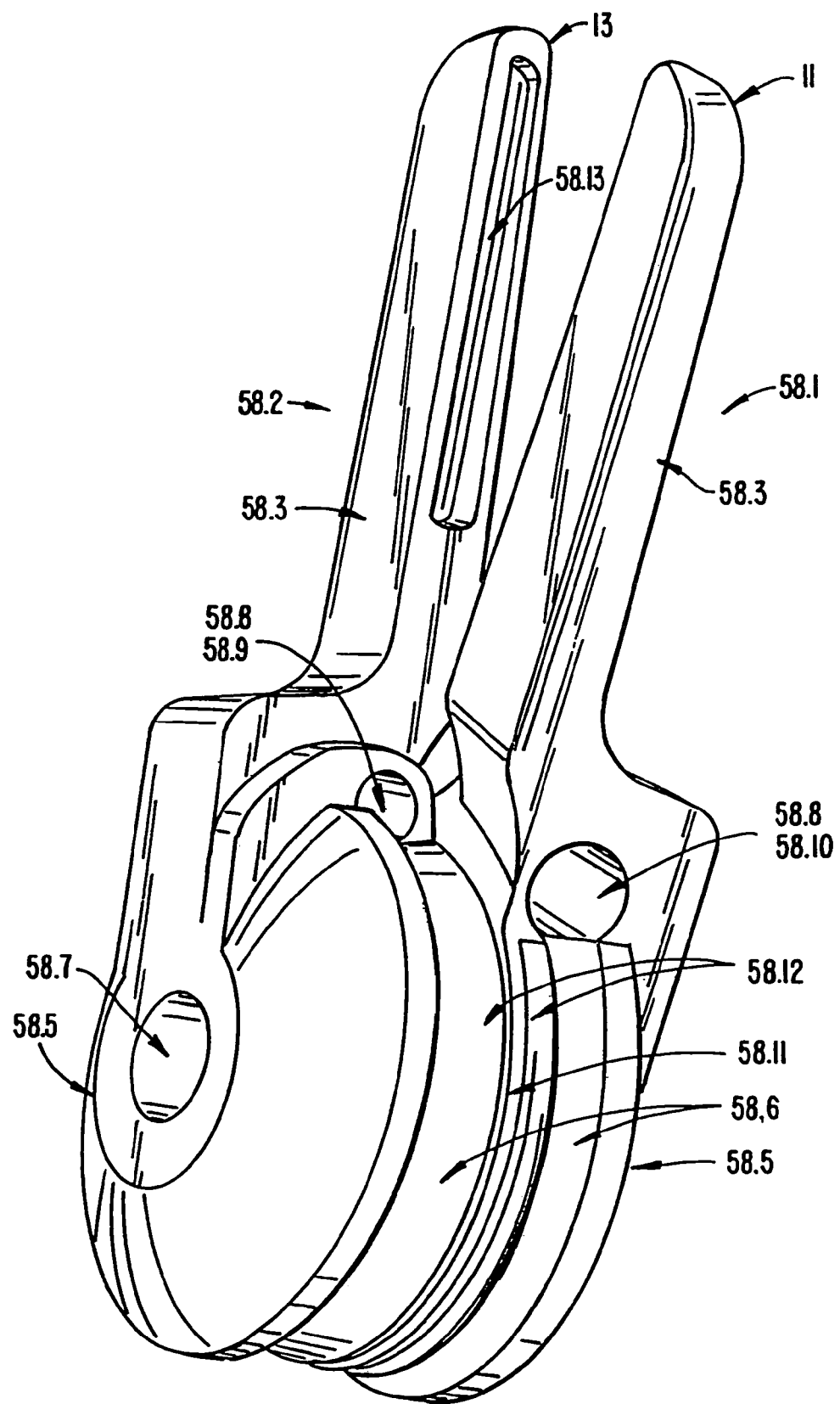
FIG. 7 is a perspective view of a clip applier end effector in accordance with the invention.
Figure 8:
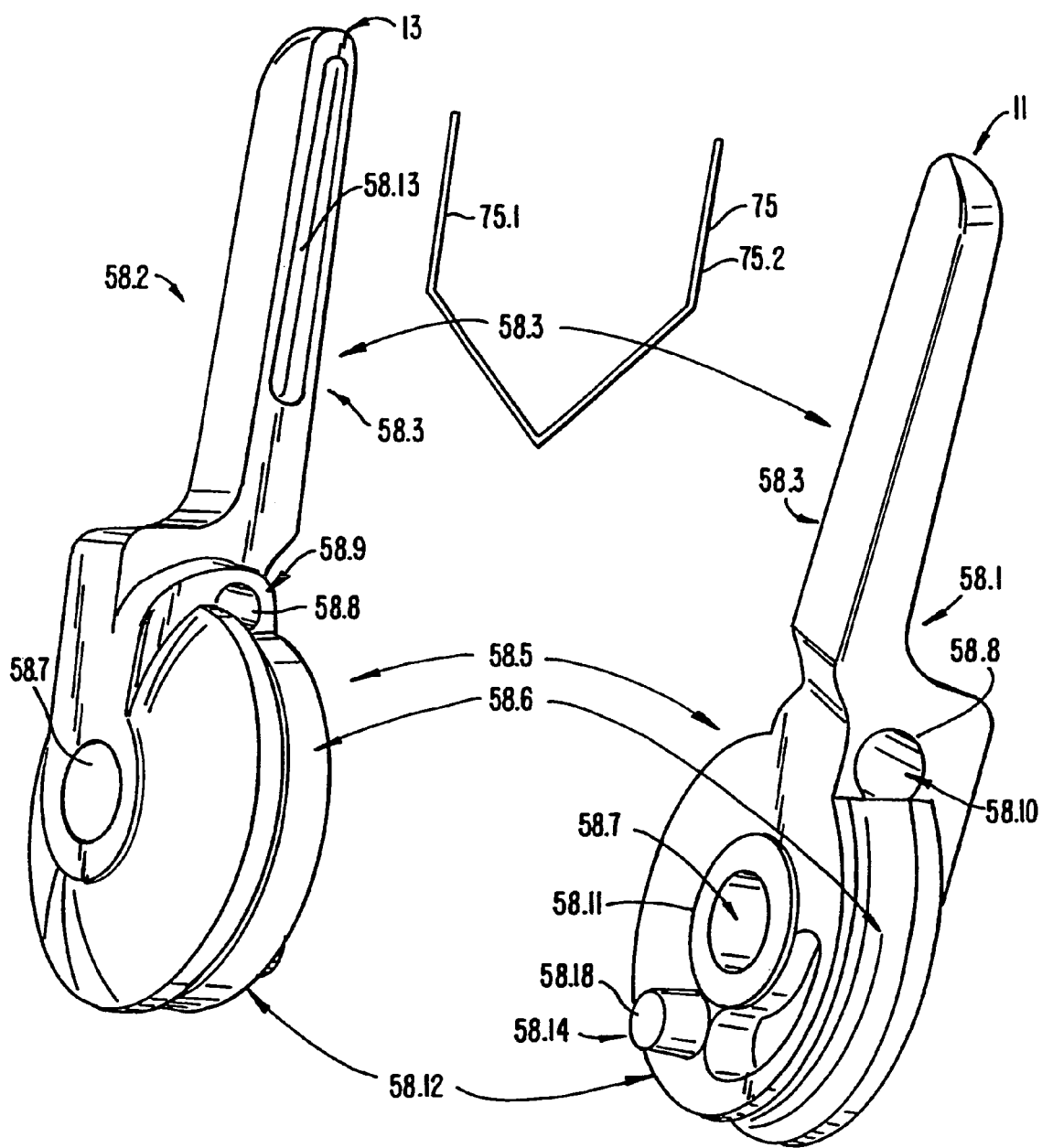
FIG. 8 is an exploded view of the clip applier end effector shown in FIG. 7.
Figure 9:
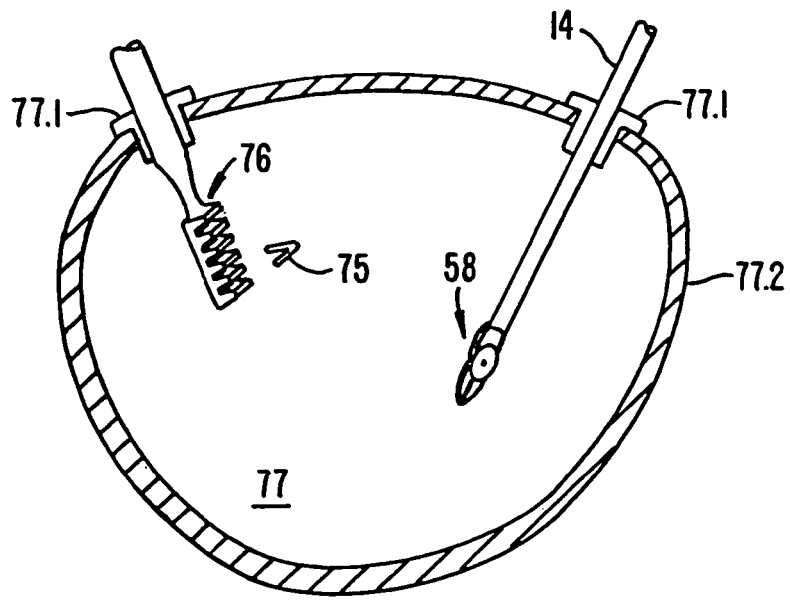
FIG. 9 is a schematic view of a clip cartridge for supplying clips in vivo to a clip applier.

FIGS. 7 and 8 show in greater detail the clip applier end effector 58 for the tool 14 of FIG. 5. The parts 58.1, 58.2 of the end effector 58 are typically the same so as to keep production costs low. Accordingly, the parts 58.1, 58.2 each include an elongate finger portion or end effector element 58.3. The finger portion 58.3 is integrally formed with an end effector mounting formation in the form of, e.g., a pulley portion 58.5. The pulley portion 58.5 defines a circumferentially extending channel 58.6 in which an elongate element in the form of, e.g., an activation cable, is carried, as described in greater detail herein below.

The pulley portion 58.5 includes an axially extending, centrally disposed hole 58.7 through which a pivot pin of the pivotal connection 60 extends. A generally circumferentially directed hole 58.8 extends through a nape region of the finger portion 58.3 and generally in register with the circumferentially extending channel 58.6. The hole 58.8 has a first portion 58.9 and a second portion 58.10 having a diameter greater than the first portion 58.9. In use, the activation cable has a thickened portion along its length which seats in the hole portion 58.10, the rest of the activation cable then extending along the channel 58.6 in opposed directions. The thickened portion is crimped in its seated position in the hole portion 58.10 so as to anchor the cable in the hole 58.8. It will be appreciated that a greater force is necessary to clamp the free ends together when gripping an object therebetween, than that which is required to open the free ends 11, 13. Thus, the thickened portion of the cable is urged against an annular stepped surface between the hole portion 58.9 and the hole portion 58.10, when the free ends 11, 13 are urged into a closed condition. The part 58.1, 58.2 has an operatively inwardly directed face 58.11 which rides against the face 58.11 of the other one of the parts 58.1, 58.2.

In use, a clip 75, as indicated in FIG. 8, is positioned between the finger portions 58.3. Opposed limbs 75.1, 75.2 of the clip 75 are positioned in longitudinally extending recesses or seats 58.13 in each of the finger portions 58.1, 58.2. It is important that the clip is securely seated in the clip applier 58 until the clip applier is caused to anchor the clip in position. If the clip 75 is not securely seated, the clip 75 could become dislocated from the clip applier 58. In such a case, valuable time could be lost in trying to find and recover the clip 75 from the surgical site. To cause the clip 75 to seat securely on the clipper pliers 58, the portions 58.1 58.2 are biased or urged in a closing direction so as to clamp the clip 75 in the opposed seats or recesses 58.13. The biasing or urging arrangement to cause such clamping of the clip 75 in the seats 58.13, as well as the mechanisms for operating the clip applier end effector 58, are discussed in detail in U.S. application Ser. No. 09/398,958, entitled "Surgical Tools for Use in Minimally Invasive Telesurgical Applications", filed on Sep. 17, 1999, the entirety of which is herein incorporated by reference. Alternatively, as described in the '958 application, instead of being urged or biased towards each other, portions 58.1 and 58.2 can be constructed in such a way (with open-ended recesses 58.13) as to open (e.g., against mechanical stops) to a predetermined angular position slightly less than the angle of the clips to be used. Thus, the natural resistance of the clip to deformation provides sufficient friction when loaded into the clip applier that a separate biasing means is unnecessary.

Normally, in use, the clip applier having the end effector 58 is removed from the surgical site, a clip 75 is then positioned between the finger portions 58.3, and then the end effector 58 is reintroduced into the patient's body so as to apply or anchor the clip 75 where required. To apply the clip, the master controls are manipulated to cause the clip applier to close so as to bend the clip 75. When the clip 75 has been applied, the end effector 58 can again be opened and removed from the surgical site, another clip 75 can then be positioned between the finger portions 58.3, and the end effector can again be introduced to the surgical site to apply that clip and so on, until all the required clips have been applied or anchored in position. This process is time-consuming.

In accordance with an embodiment of the present invention, the clips 75 are introduced into the surgical site 77 in a cavity of a patient by a dedicated surgical accessory support in the form of a cartridge 76. The end effector 58 of the clip applier can be manipulated servo mechanically or manually from outside the cavity to load a clip 75 from the cartridge 76 and affix the clip 75 to a target tissue inside the cavity. The end effector 58 need not be removed from the surgical site 77 for loading the clip 75 and reintroduced into the surgical site 77.

Figure 10:
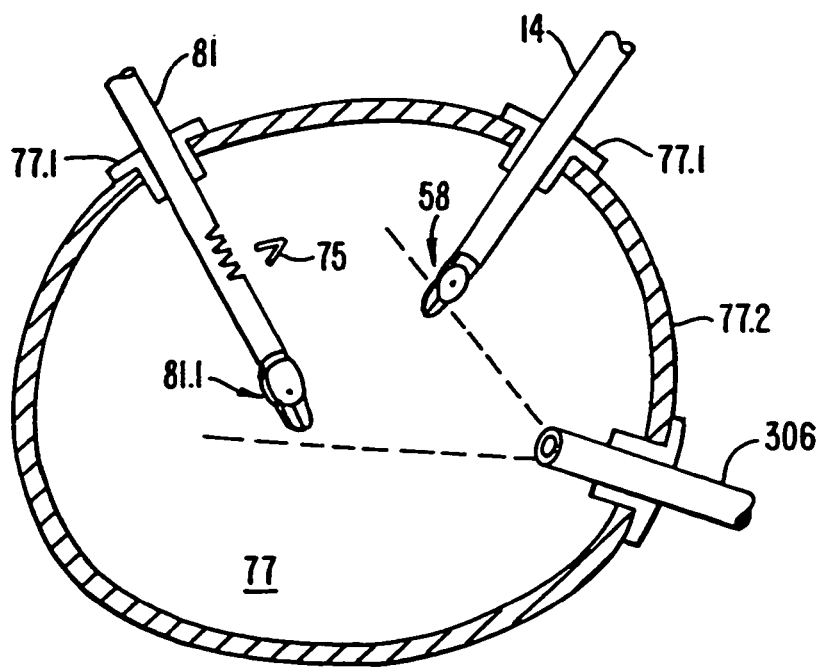
FIG. 10 is a schematic view illustrating supply of clips in vivo by another surgical tool in the surgical site.

In another embodiment shown in FIG. 10, the clips 75 are supported on the shaft of another tool 81 having an end effector 81.1 in a "piggyback" arrangement, thereby eliminating the need to open a separate port for introducing a dedicated accessory support into the surgical site 77. Cannula sleeves 77.1 are typically provided through the wall 77.2 of the patient's body for introducing the surgical tools and accessory support into the surgical site 77.

As can be understood with reference to FIG. 10, releasably mounting a surgical accessory (such as clip 75) to a robotically controlled structure (such as tool 81) may facilitate mating of the accessory with tool 14. Tool 81 can be easily and accurately positioned in a field of view of scope 306 for loading the clip applier 58. Tool 14 and/or tool 81 may be positioned and moved to accurately transfer clip 75 from tool 81 to clip applier 58 within the field of view from the scope using the robotic servomechanism to generate the desired clip loading forces, without having to verbally coordinate hand movements of two different persons.

B. Single Working Member Accessories

Another type of accessory is a single working member accessory such as a blade, a scalpel, a dissection finger, or an electrode, which does not require the more complex mechanisms for manipulating multiple working members such as forceps and clip appliers. For instance, the single working member accessory can be grasped by jaw-like working members such as forceps on a tool which can be used for manipulating different single working member accessories and providing them with the desired degrees of freedom of movement to perform different treatments on tissues in the surgical site.

Figure 11:
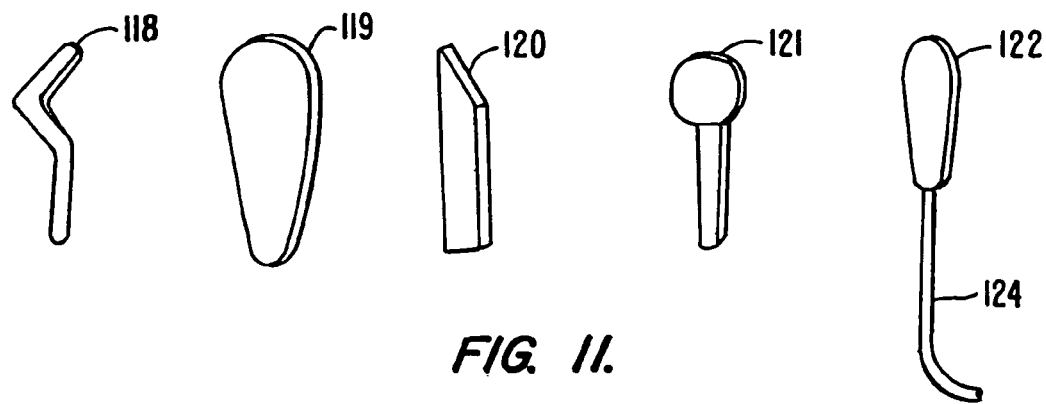
FIG. 11 is a perspective view showing examples of different single working member accessories.

FIG. 11 shows examples of single working member accessories, including a cautery or electrosurgical hook 118, a cautery blade 119, a scalpel 120, and a dissection finger 121 or Kittner for blunt dissection. Another example of a single working member accessory is an electrocautery electrode 122 used to generate an electrical current at a surgical site so as to burn or seal, e.g., ruptured blood vessels. In use, the patient is earthed and a voltage is supplied to the electrode 122. An electrically conductive cable 124 is connected to the electrode 122. In use, the cable 124 couples the electrode 122 to an appropriate electrical source outside the surgical site, preferably through an accessory body wall port. The conductive cable 124 is typically sheathed in an insulative material such as, e.g., TEFLON™. The electrode, in the form of a blade or hook, e.g., or other accessories may be dangled into the patient's body cavity through a body wall port by way of the cable and/or an associated spring mechanism, as disclosed in the context of FIGS. 16 and 18A. Grasping tool can be used to grasp one of the single working member accessories and manipulate its movement to treat the target tissue. Exemplary electrosurgical implements are disclosed in U.S. application Ser. No. 09/415,568, entitled "Minimally Invasive Surgical Hook Apparatus & Method for Using Same," filed on Oct. 8, 1999, the entirety of which is herein incorporated by reference.

It will be appreciated that should the distance between the electrode 122 and the patient be relatively great when a voltage is applied, current may jump from the electrode 122 to other conductive parts of the instrument. In such a case, current can be passed from the grasping tool to the patient along a path of least resistance, e.g., at the entry port coincident with the center of rotation 49 (see FIGS. 2A and 2B). This may cause unnecessary burning at the entry port. One way of avoiding such current flow is to insulate the electrode 122 from the grasping tool so as to inhibit current leakage from the electrode 122 to the tool. Accordingly, the components of the grasping tool may be made of non-conductive material such as, e.g., ULTEM™ or VECTRAN™. The shaft of the tool is typically made entirely from a nonconductive material, or at least sheathed in such a material, to insulate the shaft from the patient, in particular in the region of the port of entry. The preferred nonconductive material for the shaft 114.1 comprises an electrical grade fiberglass/vinyl ester composite material. A shaft of stainless steel or carbon fiber may be coated with, e.g., a nylon or parylene, such as Nylon-11 or Parylene C.

Figure 11A:
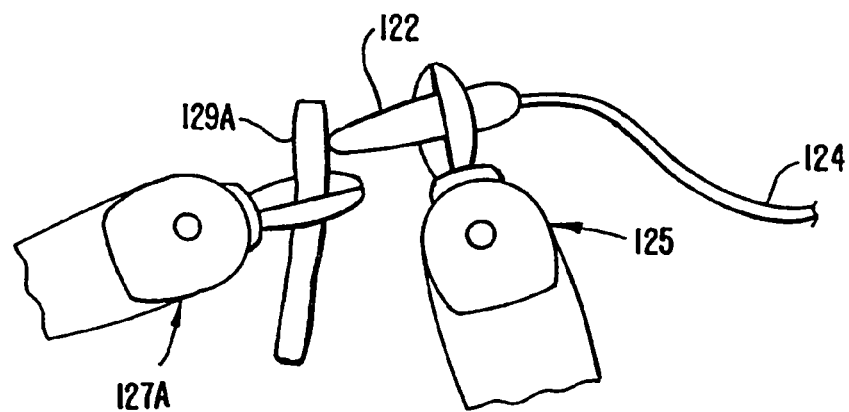
FIG. 11A is a schematic view illustrating a way of performing electrocautery.

FIG. 11A shows one way of performing electrocautery with superior safety and precision. The electrode 122 is grasped by a grasping tool such as forceps 125 having insulative components for making contact with the electrode 122. Alternatively, the electrode 22 can be partially sheathed in nonconductive material for making contact with the other tool. Another tool 127A is used to hold a tissue such as a vessel 129A. The portion of the tool 127A in contact with the tissue 129A is electrically conductive. The electrode 122 is coupled with one lead of a bipolar system, while the grasping tool 127A holding the tissue 129A is coupled with the other lead of the bipolar system. The electrode 122 is an active electrode and the tool 127A is a passive electrode. The tissue disposed between the active and passive electrodes complete the electrical circuit of the bipolar system. When sufficient power is introduced, coagulation of the tissue between the electrode 122 and the tool 127A occurs.

Figure 11B:
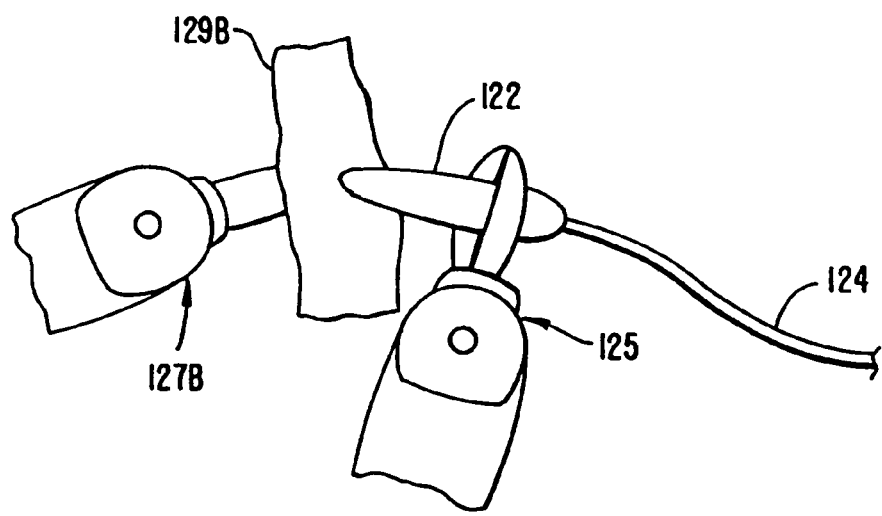
FIG. 11B is a schematic view illustrating another way of performing electrocautery.

In another embodiment shown in FIG. 11B, the tool 127B is placed behind the target area of the tissue 129B, while the electrode 122 approaches the target area from the front to define a specific coagulation zone. In both FIGS. 11A and 11B, the coagulation zone for the tissue 129B is well-defined to provide safe, direct electrocauterization.

Figure 12:
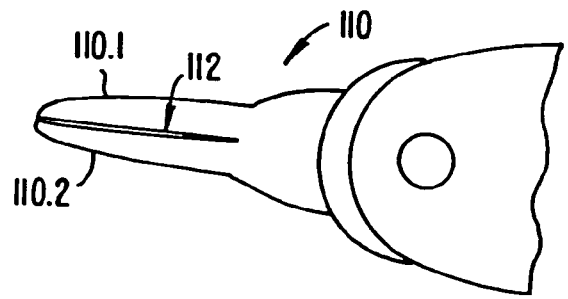
FIG. 12 is a side view of forceps.

FIG. 12 shows an example of a grasping tool having forceps 110 for grasping and manipulating one of the single working member accessories inside the surgical site. The forceps 110 is mounted on a wrist mechanism similar to the wrist mechanism 50. The forceps 110 has two working members 110.1, 110.2. The working members 110.1, 110.2 are slightly bent to define a space 112 between them. In use, it is difficult to provide force feedback to the master controls. Thus, it could happen that an organ, or tissue, or the like, can be grasped by forceps with too much force which may unnecessarily damage such organ or tissue. To inhibit this, the space 112 is provided. The members 110.1, 110.2 have a degree of resilience. Thus, when the forceps is used, the surgeon manipulating the master controls can obtain an indication of the force applied when grasping with the forceps 110 by visually monitoring resilient deflection of the members 110.1, 110.2 relative to each other, all as described in application Ser. No. 09/398,958.

The single working member accessories can be introduced into the surgical site in any suitable way. For instance, each accessory can be connected to a cable and inserted through an opening into the surgical site and be removed from the site by pulling on the cable from outside the patient's body. Alternatively, an accessory support can be used to introduce a plurality of accessories into the surgical site.

Figure 13:
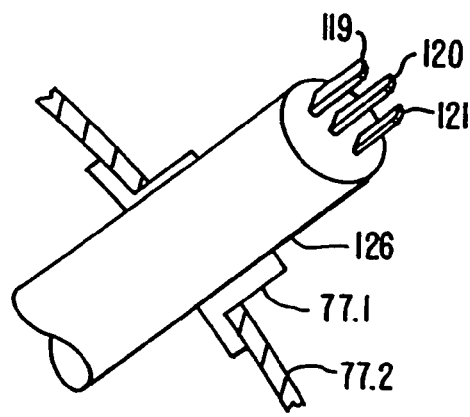
FIG. 13 is a perspective view of a surgical accessory support block according to an embodiment of the invention.

FIG. 13 illustrates a surgical accessory support in the form of a block 126 for holding the accessories such as the cautery blade 119, scalpel 120, and dissection finger 121. The block 126 is introduced through the cavity wall 77.2 via a cannula sleeve 77.1. The support block 126 in one embodiment is made of a foam material or the like which deflects to releasably secure the accessories therein. The accessories can be removed by the grasping tool 110 inside the surgical site to perform a desired treatment and then returned to the block 126 after use. The block 126 is particularly suitable for supporting sharp objects such as blades and scalpels.

Figure 14:
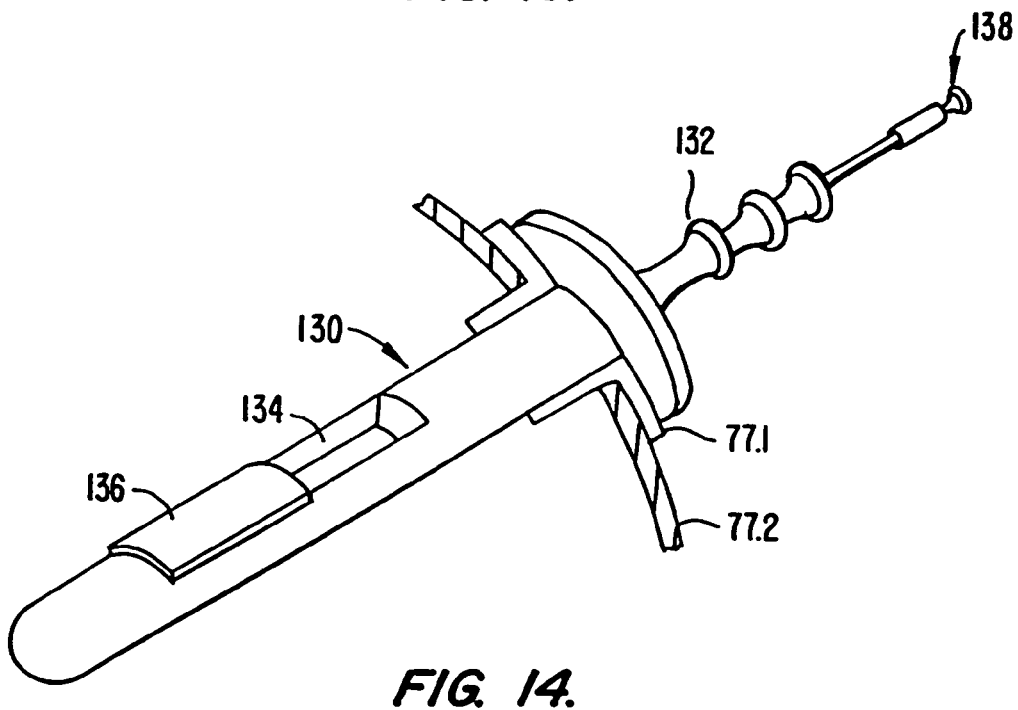
FIG. 14 is a perspective view of a surgical accessory container according to another embodiment of the invention.

FIG. 14 shows a container or box 130 as another embodiment of a surgical accessory support. The box 130 extends through the cavity wall 77.2 via a cannula sleeve 77.1. A handle 132 supports the box 130 in the surgical site from outside the patient's cavity. The box 130 includes a compartment 134 for housing accessories and a door 136 which can be opened to allow access to the accessories, and be closed during transportation of the box 136 into and out of the surgical site. A variety of mechanisms can be used to control movement of the door 136. In the embodiment shown, a control rod 138 is connected with the door 136 and extends through the end of the handle 132. The control rod 138 allows the operator to open the door 136 by pushing the rod 138 toward the handle 132 and to close the door 130 by pulling the rod 138 away from the handle 132. A physical or solenoid-activated latch might be included to lock the door in an open configuration during an operation, if desired. It is appreciated that other devices can be used for introducing the surgical accessories into the surgical site and supporting them therein.

Figure 15A:
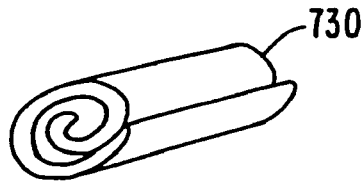
FIG. 15A is a perspective view of a surgical accessory support belt in a deflated state according to another embodiment of the invention.
Figure 15B:
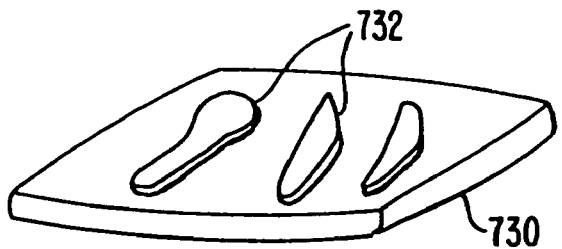
FIG. 15B is a perspective view of the surgical accessory support belt of FIG. 15A in an inflated state.

In another embodiment as shown in FIG. 15A, an inflatable tool belt or support 730 can be used to hold accessories 732 such as needles, gauze, or blades, and can be inserted into the surgical site through a port with the tool belt 730 in a deflated state. The accessories 732 may be releasably attached to the tool belt 730 in any suitable manner, such as the use of velcro or the like. After the tool belt 730 has been inserted into the surgical site, it can be inflated in a manner similar to a balloon catheter to expose the accessories 732 so that they may be used in the surgical site, as illustrated in FIG. 15B. The inflated tool belt 730 provides support for the accessories 732 and may cause the accessories to stand in an erect position, making them more easily graspable by a grasping tool such as forceps 110 or the like. The tool belt 730 can be deflated for retraction. A mechanism similar to those used for balloon catheters can be used for inflating and deflating the tool belt 730.

Single working member end effectors, such as a blade or a scalpel on a surgical tool can also be replaced inside the patient without removing the tool from the patient's body cavity. Mechanisms allowing such replacement include, e.g., a blade mounted on a pliable polymeric sleeve that fits snugly over a finger-like projection.. For replacement, the tool is simply loosened and attached to an accessory belt of the type disclosed herein, and replaced with another single member tool having a similar sheath mounting structure. Alternative methods of mounting single member tools to the end of a robotic tool are disclosed in FIGS. 17-19 of U.S. application Ser. No. 09/398,598, which is incorporated herein by reference in its entirety.

C. Tool Tip Accessories

Figure 16:
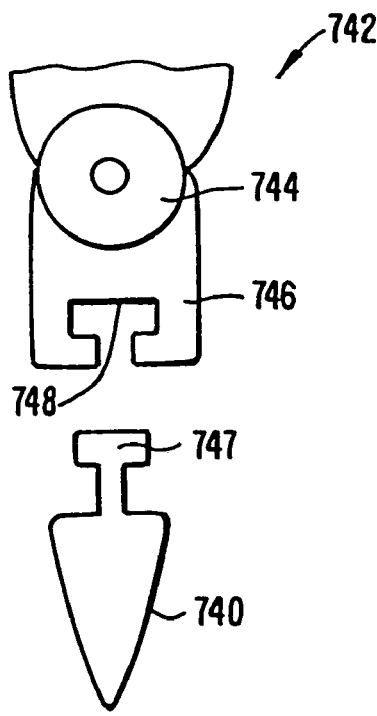
FIG. 16 is an elevational view of a tool tip for a single working member end effector according to another embodiment of the invention.

FIG. 16 shows an example of a removable tool tip 740 for a single working member end effector 742 having a drive pulley 744 connected with a tool end 746. The tool tip 740 is one of a plurality of tool tip accessories that can be introduced separately into the surgical tool so that the end effector 742 can be fitted with different tool tips for performing different procedures as desired without having to leave the surgical site. Examples of tool tips include blades, scalpels, electrodes, and the like. The tool tip 740 and the tool end 746 are configured to form a mating connection. The tool tip 740 can be grasped by a grasping tool and be snapped or wedged onto the tool end 746. In the embodiment shown, the tool tip 740 has a protrusion 747 that detachably fits into a slot or recess 748 of the tool end 746. To remove the tool tip 740, the grasping tool can be used to grasp the tool tip 740 and disengage it from the tool end 746. It is understood that other detachable mechanisms may be used for connecting the tool tip 740 with the tool end 746 including, for example, cantilever-type snaps or the like.

Figure 17:
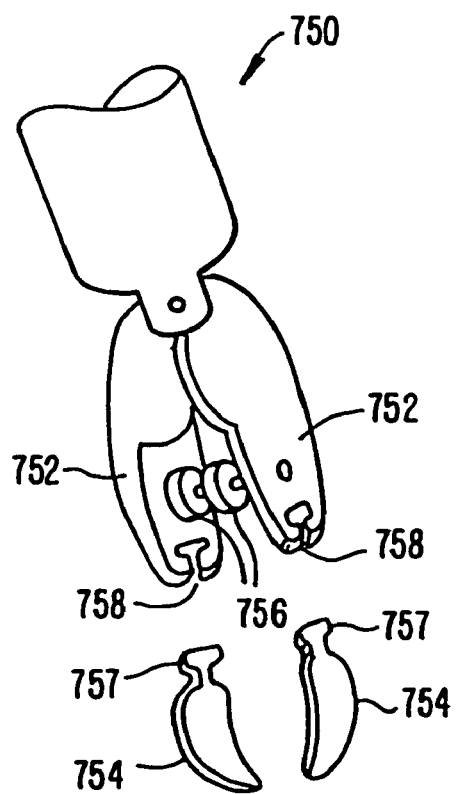
FIG. 17 is a perspective view of a pair of tool tips for a double working member end effector according to another embodiment of the invention.

In FIG. 17, a double working member end effector 750 has a pair of tool ends 752 that can be fitted with two tool tips 754 by mating protrusions 757 of the tool tips 754 with slots 758 of the tool ends 752. A pair of drive pulleys 756 are connected with the tool ends 752 to move the tool tips 754 in a jaw-like arrangement. The tool tips 754 may include sets of forcep tips or other jaw-like working member tips of varying sizes or shapes.

Figures 18A, 18B:
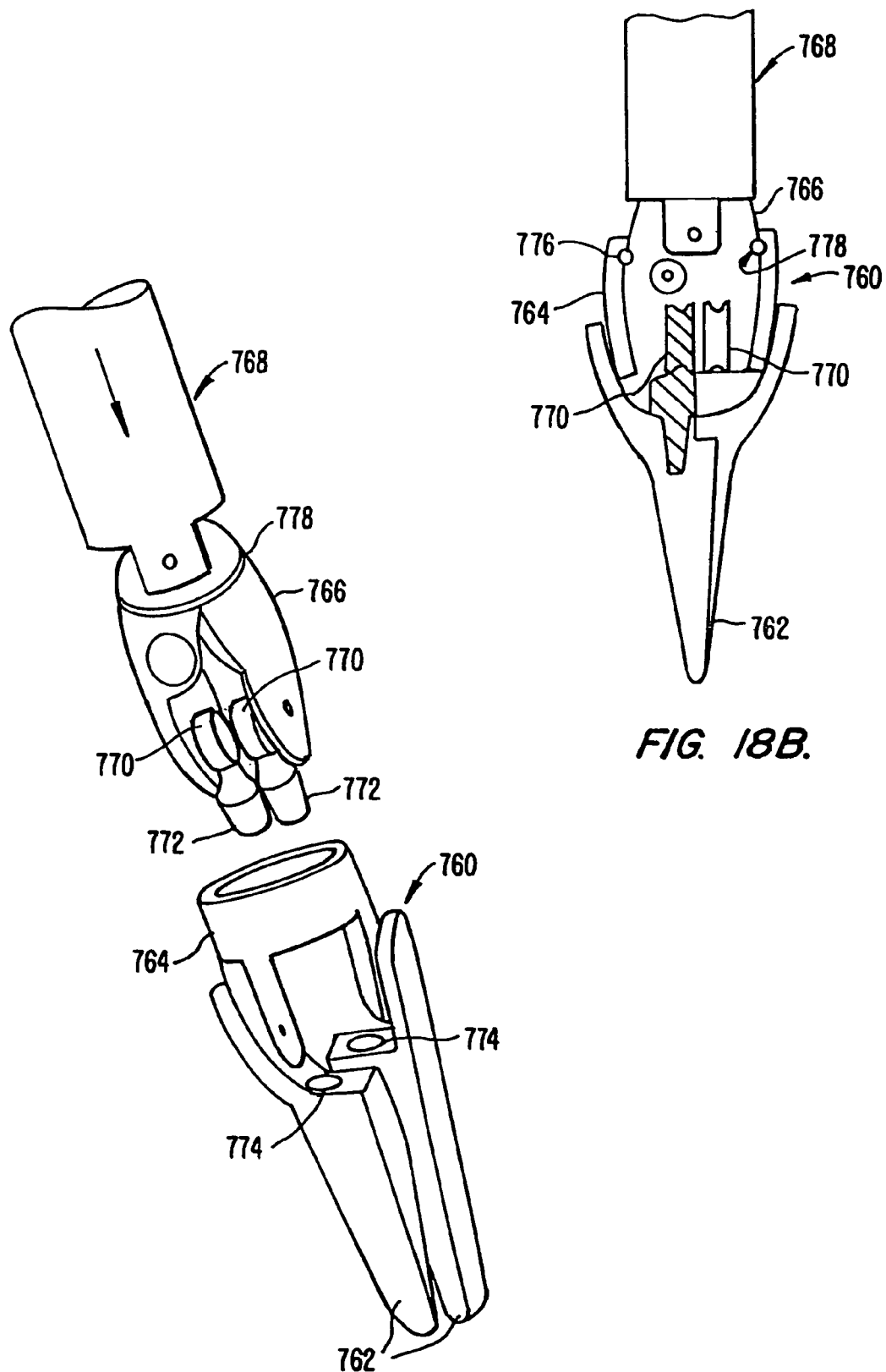
FIG. 18A is a perspective view of a dual tip tool glove for a double working member end effector according to another embodiment of the invention.
FIG. 18B is a partial cross-sectional view of the dual tip tool glove assembled with the double working member end effector of FIG. 18A.

Another way to provide different tool tips for a double working member end effector is to use a dual tip tool glove 760 as illustrated in FIGS. 18A and 18B. As shown in FIG. 18A, the tool glove 760 includes a pair of fingers 762 that are pivotally attached to a tool glove support or collar 764. The collar 764 is a hollow member configured to be placed over the wrist member 766 of a double working member end effector 768. The wrist member 766 supports a pair of drive pulleys 770 that are connected to a pair of tool ends or nubs 772. The tool nubs 772 are inserted into a pair of openings 774 of the pair of fingers 762 of the tool glove 760 when the tool glove 760 is joined with the wrist member 766 in the attached position shown in FIG. 18B. The pulleys 770 are actuatable (typically by cables) to rotate the tool nubs 772 which in turn cause the fingers 762 to rotate and to move, e.g., in a jaw-like manner.

The collar 764 is configured to be releasably locked onto the wrist member 766. As best seen in FIG. 18B, the collar 764 includes a spring retention ring 776 which applies a resilient force to wrap around a groove 778 on the wrist member 766 to resiliently lock the collar 764 onto the wrist member 766 in the attached position. The spring retention ring 776 is typically a metal ring held in a groove in the collar 764, and can split to expand in diameter and allow the collar 764 to be placed over the wrist member 766. A grasping tool may be used to manipulate the tool glove 760 for assembly with the wrist member 766. When the retention ring 776 reaches the groove 778 on the wrist member 766, it contracts around the groove 778 from the split position, thereby releasably locking the collar 764 onto the wrist member 766. To disconnect the tool glove 760 from the wrist member 766, a sufficient pulling force is applied to the tool glove 760 via the grasping tool to overcome the resilient force of the retention ring 776. It is appreciated that other releasable locking mechanisms may be used for locking the tool glove 760 onto the wrist member 766 of the end effector 768. Further, the fingers 762 of the tool glove 760 may have other configurations.

Figure 6D:
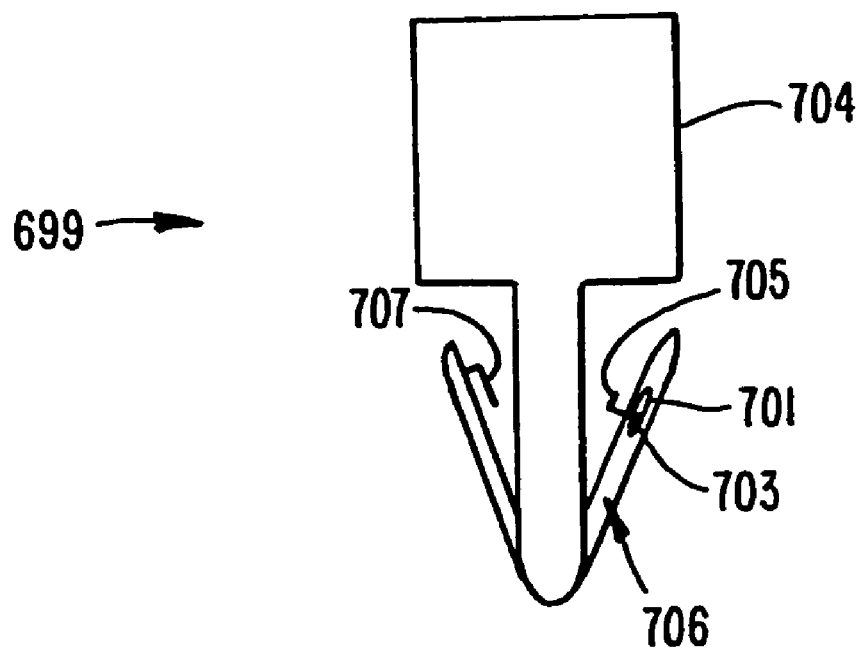
FIGS. 6D and 6E depict a preferred embodiment of the master control device shown in FIGS. 6A-6C having a locking mechanism for locking the slave end effector into an actuated position.
Figure 6E:
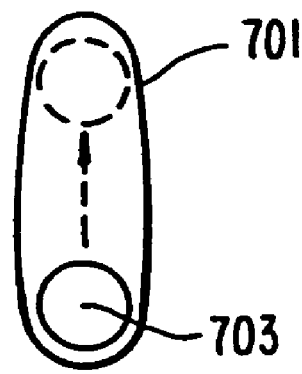

It has been found that when a surgeon uses a grasper to grab and hold an accessory tool for an extended period of time to perform surgery, in the manner previously described, the surgeon at some point may wish to relax his grip on the master control without the grasper losing its grip on the accessory tool. Further, the surgeon may wish to operate using the accessory tool without having to constantly grip the master control to actuate the grasper to grip the accessory. This ability to avoid constantly having to actuate two-member tools to close/grip is also desirable, e.g., during suturing, when the surgeon may need to exert a large gripping force on a needle while manipulating the needle to sew tissue. Such maneuvers sometimes can prove awkward and tiring to the surgeon's hands if too much gripping in involved over a long period of time. This problem is addressed by providing the surgeon with the ability to "lock" the graspers closed, after actuation, so that the graspers remain closed and gripping, e.g., a needle or accessory tool until the surgeon commands the graspers to do otherwise. Locking the two-membered tool in a closed/gripping position allows the surgeon to relax his gripping pressure on the master control after actuation of the tool. This functionality can be implemented in any number of ways, such as by the surgeon physically- or voice-activating a switch or button or latch on the master control while the tool is actuated, to instruct the system to maintain the tool's actuation until a further command is received, or by programming the control computer to detect when the operator intends to actuate the virtual locking function, e.g., by detecting a threshold closing force on the masters applied over a specific period of time, such as two seconds. Several threshold forces, corresponding to several different closing/locking forces might be provided as desired. Once the command is given, the computer would lock that particular tool into position and either maintain the particular force applied by the surgeon at the time the locking command was provided, or would maintain a maximum gripping force (depending upon how the system is configured) without further gripping force from the surgeon on the corresponding master control, until a further "unlock" command is given. Upon activation in this manner, the surgical system preferably would provide the surgeon with a perceivable indication that the tool was locked, e.g., through an audible sound, illumination of a locking light, illumination of an icon on the surgeon s console screen, etc. One example of a latch locking mechanism is shown in FIG. 6D. Sliding button 703 in slot 701 has two positions, as more clearly seen in FIG. 6E. When in a first position, latches 705 and 707 do not catch when the pincher formation 706 is closed. When in a second position, however, latches 705 and 707, preferably made of a resilient metal such as spring steel (similar to the latching mechanism on the Castro-Viejo Needle Drivers made by Scanlan), do catch, thereby keeping the master locked into position and the slave end effector actuated until released. In this embodiment, the pincher formation remains in a closed profile. If desired, the end effector could be locked as described above while leaving the surgeon free to continue to manipulate the pincher formation as before—e.g., for comfort reasons—but without giving the surgeon the ability to further affect the actuation of the end effector until "unlocking" the mechanism.

The tool is preferably unlocked in similar manner by a threshold outward force on the master actuation controls, or activation of a separate button or voice control. Upon unlocking, the surgeon would again be able to control the end effector as before, and preferably would be provided with an indication from the system that the unlock command had been received, such as another audible or visual signal or elimination of the previously illuminated icon.

D. Sheath Accessories

Sheath accessories can be used to modify the working members of a surgical tool. For instance, a pair of jaw-like working members such as forceps on the working end of a tool can be fitted with insulating sheaths or resilient sheaths when desired.

Figure 19:
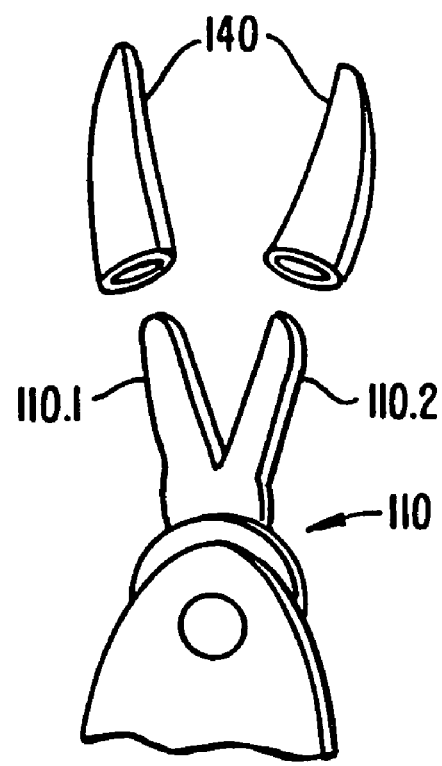
FIG. 19 is an exploded perspective view of insulative or resilient sheaths for forceps.

FIG. 19 shows forcep sheaths 140 configured to fit over working members 110.1, 110.2 of forceps 110, forming a mated connection therewith. For insulation, the forcep sheaths 140 are made of an insulative material such as rubber, VECTRAN™, ULTEM™, or the like. In an alternative embodiment, the forcep sheaths 140 are made of a resilient material such as an elastomer for protecting tissues from damage caused by excessive pressure exerted by the forceps 110. The surgeon can visually monitor the deformation of the resilient sheaths 140 and adjust the gripping force accordingly. The sheaths 140 can be introduced into the surgical site by the container of FIG. 14, and be placed over the forceps 110 while inside the body cavity using another grasping tool, for example.

E. Other Accessories

Figure 20:
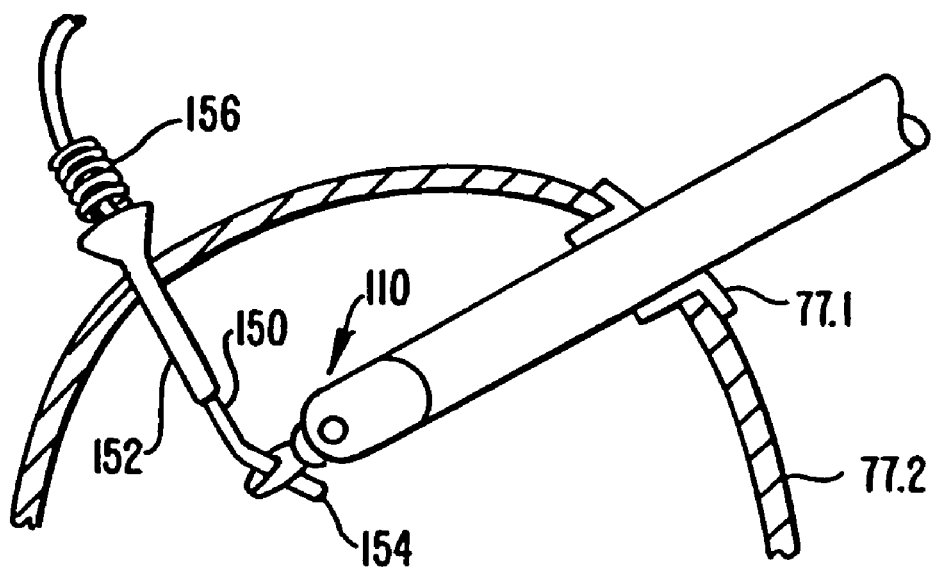
FIG. 20 is a schematic view illustrating manipulation of an in vivo flow tube by a grasping tool.

Another example of an accessory is a flow tube 150 introduced into the cavity of the patient for providing suction, introducing a gas or a liquid, or transporting other matters into or out of the cavity, as shown in FIG. 20. The flow tube 150 can be grasped, for example, by a grasping tool having forceps 110 inside the cavity and moved to the desired location for treating a particular area of the patient's body.

In FIG. 20, the flow tube 150 is inserted through the cavity wall 77.2 of a patient into the cavity via a tube support 152. The flow tube 150 is typically flexible. The flow tube 150 includes an opening 154 at a distal end. The flow tube 150 can be connected with a vacuum source to provide suction to draw out fluid or other matters from the cavity through the opening 154, or an external source for introducing a fluid in the form of a liquid such as saline or a gas such as $CO_2$ into the surgical site, or the like. In one embodiment, the flow through the opening 154 of the tube 150 can be modulated by adjusting the grip of the grasper on the tube 150.

To minimize interference with the manipulation of tools in the surgical site, the flow tube 150 is advantageously resiliently biased by a spring 156 to return to the location near the tube support 152 at the aperture of the cavity wall 77.2. The spring 156 compresses when the tube 150 is pulled further into the surgical site and causes the tube 150 to automatically return closer to the wall aperture when the tube 150 is released by the forceps 110. In this way, the flow tube 150 stays clear of the remaining area of the surgical site. It is appreciated that other suitable resilient mechanisms may be employed, and that a similar resilient mechanism can be adapted for use with other accessory introducing devices.

Figure 21:
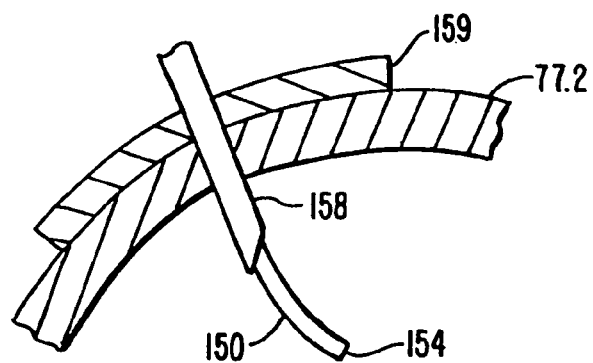
FIG. 21 is a schematic view illustrating introduction of an in vivo flow tube into the surgical site using a needle.

In some cases, the tube 150 is sufficiently small that the tube support 152 is no larger in cross-section than a typical hypodermic needle. FIG. 21 shows the use of a hollow needle 158 for introducing the flow tube 150 into the internal cavity 77. A pad 159 is affixed to the external surface of the cavity wall 77.2 of the patient. The pad 159 is typically made of a rubber or foam-like material, and may include a self-adhering surface for affixing to the external surface. The needle 158 pierces through the pad 159 and cavity wall 77.2 carrying the flow tube 150 through its core into the cavity 77. In a specific embodiment, the needle is a small gauge Veress needle.

Figure 22:
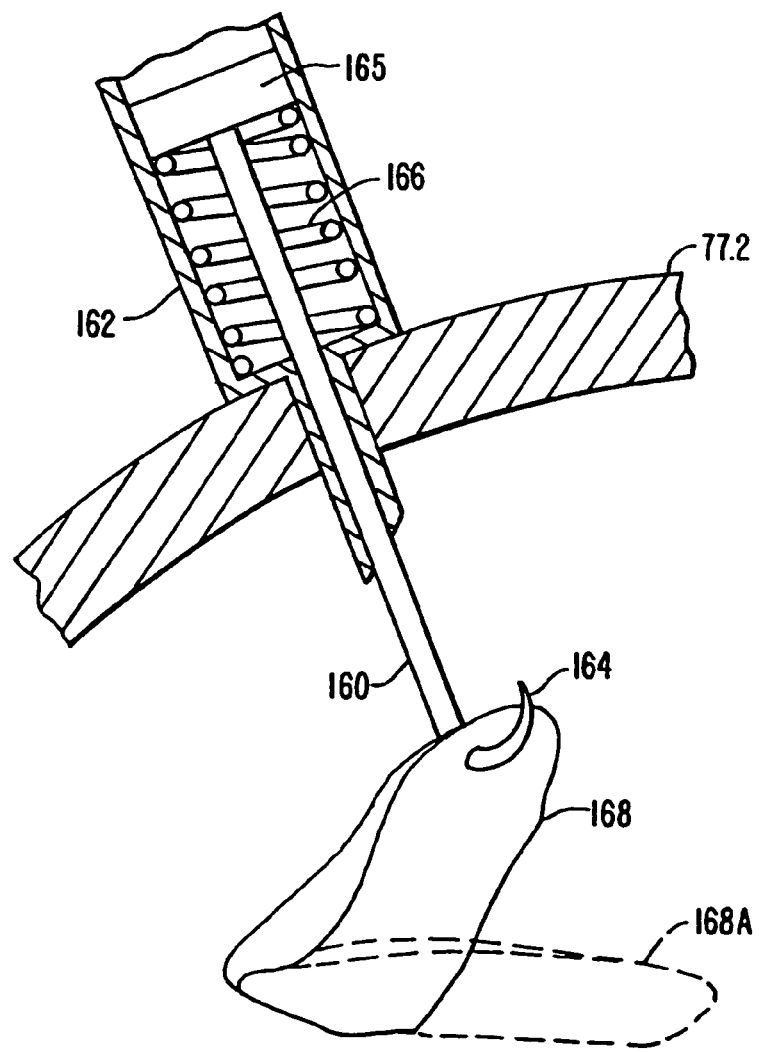
FIG. 22 is a schematic view illustrating an in vivo retraction member.

Another example of an accessory is a retraction member 160 introduced through the cavity wall 77.2 of a patient via a support housing 162 for retracting tissue or the like, as illustrated in FIG. 22. The distal portion of the housing 162 which extends through the cavity wall 77.2 is desirably small to minimize the size of the incision. In a specific embodiment, the distal portion of the housing 162 is as small as a 12 gage needle. The retraction member 160 includes a gripping portion such as a hook 164 or the like for securing a tissue 168 or other objects inside the cavity. The retraction member 160 is connected with a piston 165 which is slidably disposed in the support housing 162. A spring 166 biases the piston 165 away from the cavity wall 77.2 and, as a result, biases the retraction member 160 toward the distal portion of the support 162 at the opening of the cavity wall 77.2. The retraction member 160 can be grasped, for example, by a grasping tool inside the cavity to secure the tissue 168 with the hook 164. When the retraction member 160 is released, the biasing force of the spring 166 returns the retraction member 160 to the position nearer the opening of the cavity wall 77.2, thereby retracting the target tissue 168 from its original location indicated at 168A. The displacement of the tissue 168 exposes the desired target area for treatment.

The above-described arrangements of apparatus and methods are merely illustrative of applications of the principles of this invention and many other embodiments and modifications may be made without departing from the spirit and scope of the invention as defined in the claims. For instance, other telesurgical systems, e.g., without a remote center of motion, and surgical tools can be used to perform surgery with the in vivo accessories. The examples of surgical accessories and ways of presenting them in vivo are illustrative and not exhaustive. Additional illustrative examples of surgical accessories that can be provided in vivo in accordance with the present invention include various gauge needles and/or threads or sutures, gauze, and the like. The scope of the invention should, therefore, be determined not with reference to the above description, but instead should be determined with reference to the appended claims along with their full scope of equivalents.

What is claimed is:

1. An apparatus for providing a surgical accessory in vivo through a wall of a patient body into an internal cavity of the patient body for effecting a desired treatment of a target tissue in the patient body, the apparatus comprising:
   a surgical accessory;
   an accessory introducer having a proximal end and a distal end, the distal end of the introducer insertable into an opening in the patient body and adapted to introduce the surgical accessory through the opening to the internal cavity;
   a spring connected to the accessory introducer to resiliently bias the surgical accessory to a location within the internal cavity; and
   a grasping tool for grasping and moving the surgical accessory to a position in the patient for effecting the desired treatment while compressing the spring so that the spring returns the surgical accessory to the biased location upon release of the surgical accessory by the grasping tool.

2. The apparatus of claim 1 wherein the accessory introducer comprises a support member configured to be anchored to the wall of the patient body at the opening; and a slidable member coupled to the surgical accessory, the slidable member being slidable relative to the support member.

3. The apparatus of claim 2 wherein the spring is coupled to the support member and the slidable member.

4. The apparatus of claim 1 wherein the accessory introducer comprises a needle portion for piercing through the wall of the patient body into the internal cavity, the needle portion including a hollow core for introducing the surgical accessory.

5. The apparatus of claim 1 wherein the surgical accessory is a flow tube.

6. The apparatus of claim 5 wherein the flow tube is connected to a vacuum source to provide suction to draw out matter from the internal cavity through the opening.

7. The apparatus of claim 5 wherein the flow tube is connected to an external source for introducing matter into the internal cavity through the opening.

8. The apparatus of claim 7 wherein the matter is a gas.

9. The apparatus of claim 7 wherein the matter is a liquid.

* * * * *